US010662264B2

(12) United States Patent
Fei et al.

(10) Patent No.: US 10,662,264 B2
(45) Date of Patent: *May 26, 2020

(54) POLYMER COMPRISING A PLURALITY OF PHENOTHIAZINE GROUPS AND METHODS OF MAKING THE SAME

(71) Applicant: Ascensia Diabetes Care Holdings AG, Basel (CH)

(72) Inventors: Jiangfeng Fei, Sleepy Hollow, NY (US); William Chiang, Pennington, NJ (US); Frank Kerrigan, Wadebridge (GB); Stuart Green, Camelford (GB); Craig Robson, Camelford (GB); Howard Easterfield, Bude (GB)

(73) Assignee: Ascensia Diabetes Care Holdings AG, Basel (CH)

( * ) Notice: Subject to any disclaimer, the term of this patent is extended or adjusted under 35 U.S.C. 154(b) by 131 days.

This patent is subject to a terminal disclaimer.

(21) Appl. No.: 15/915,184

(22) Filed: Mar. 8, 2018

(65) Prior Publication Data
US 2018/0194877 A1    Jul. 12, 2018

Related U.S. Application Data

(60) Continuation of application No. 15/334,814, filed on Oct. 26, 2016, now Pat. No. 9,944,725, which is a
(Continued)

(51) Int. Cl.
*C08F 8/34* (2006.01)
*A61K 49/00* (2006.01)
(Continued)

(52) U.S. Cl.
CPC .......... *C08F 8/34* (2013.01); *A61K 49/0004* (2013.01); *C07D 279/08* (2013.01);
(Continued)

(58) Field of Classification Search
CPC ....................................................... C08F 8/34
(Continued)

(56) References Cited

U.S. PATENT DOCUMENTS 4,490,464 A   12/1984 Gorton
4,710,570 A   12/1987 Thien
(Continued)

FOREIGN PATENT DOCUMENTS

EP    1293574        3/2003
WO    WO2010141359   12/2010

OTHER PUBLICATIONS

International Searching Authority, "International Search Report and Written Opinion for PCT/US11/038054", dated Sep. 14, 2011, Publisher: European Patent Office, Published in: EP.
(Continued)

*Primary Examiner* — Duc Truong
(74) *Attorney, Agent, or Firm* — Nixon Peabody LLP

(57) ABSTRACT

A non-leaching mediator may include a polymer having a polymeric backbone, and a plurality of phenothiazine groups bonded to the polymeric backbone. The plurality of phenothiazine groups may include at least one of a phenothiazine group having the general formula (IV):
(Continued)

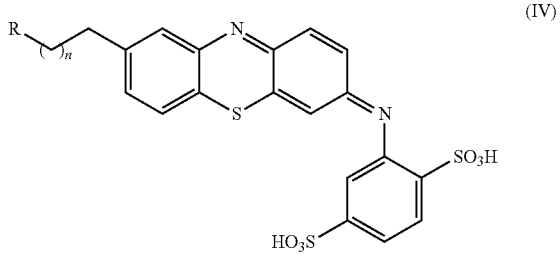

and salts thereof, where n is about 9 and "R" represents the polymeric backbone to which the phenothiazine group is bonded, and a phenothiazine group having the general formula (V):

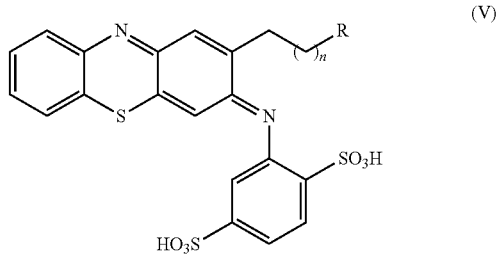

and salts thereof, where n is about 9 and "R" represents the polymeric backbone to which the phenothiazine group is bonded.

13 Claims, 12 Drawing Sheets

Related U.S. Application Data division of application No. 14/963,908, filed on Dec. 9, 2015, now Pat. No. 9,505,884, which is a division of application No. 14/259,408, filed on Apr. 23, 2014, now Pat. No. 9,238,717, which is a division of application No. 13/116,427, filed on May 26, 2011, now Pat. No. 8,742,063.

(60) Provisional application No. 61/349,469, filed on May 28, 2010.

(51) Int. Cl.
| | | |
|---|---|---|
| *C07D 279/08* | (2006.01) |
| *C08F 8/30* | (2006.01) |
| *C08G 59/40* | (2006.01) |
| *C12Q 1/00* | (2006.01) |
| *C08G 75/24* | (2006.01) |
| *C07D 279/20* | (2006.01) |
| *C08G 73/02* | (2006.01) |
| *C07D 417/14* | (2006.01) |
| *G01N 27/327* | (2006.01) |

(52) U.S. Cl.
CPC ......... *C07D 279/20* (2013.01); *C07D 417/14* (2013.01); *C08F 8/30* (2013.01); *C08G 59/4007* (2013.01); *C08G 59/4064* (2013.01); *C08G 73/024* (2013.01); *C08G 75/24* (2013.01); *C12Q 1/004* (2013.01); *G01N 27/3272* (2013.01)

(58) Field of Classification Search
USPC ......................................................... 528/419
See application file for complete search history.

(56) References Cited

U.S. PATENT DOCUMENTS

| | | | |
|---|---|---|---|
| 4,810,636 A | 3/1989 | Corey | |
| 5,089,112 A | 2/1992 | Skotheim | |
| 5,264,092 A | 11/1993 | Skotheim | |
| 5,393,615 A | 2/1995 | Corey | |
| 5,498,542 A | 3/1996 | Corey | |
| 5,520,786 A | 5/1996 | Bloczynski | |
| 5,631,371 A | 5/1997 | Bloczynski | |
| 6,605,200 B1 | 8/2003 | Mao | |
| 7,163,616 B2 | 1/2007 | Vreeke | |
| 8,742,063 B2 | 6/2014 | Fei | |
| 9,238,717 B2 | 1/2016 | Fei | |
| 9,505,884 B2 * | 11/2016 | Fei | ........................ C07D 279/08 |
| 9,944,725 B2 * | 4/2018 | Fei | ........................ C07D 279/08 |
| 2016/0083519 A1 | 3/2016 | Fei | |

OTHER PUBLICATIONS

Chemical Abstracts Service, "Chemical Structure Search", Jul. 7, 2008, pp. 1-86, Publisher: American Society, Published in: Columbus, Ohio, United States.
Chemical Abstracts Service, "Chemical Structure Search", Jul. 7, 2008, pp. 1-214 Publisher: American Society, Published in: Columbus, Ohio, United States.
Chemical Abstracts Service, "Chemical Structure Search", Aug. 5, 2008, pp. 1-75 Publisher: American Society, Published in: Columbus, Ohio, United States.

\* cited by examiner

POLYMER COMPRISING A PLURALITY OF PHENOTHIAZINE GROUPS AND METHODS OF MAKING THE SAME

REFERENCE TO RELATED APPLICATIONS

This application is a continuation of U.S. patent application Ser. No. 15/334,814 filed Oct. 26, 2016 now U.S. Pat. No. 9,944,725, which is a divisional of U.S. patent application Ser. No. 14/963,908 filed Dec. 9, 2015 and issued as U.S. Pat. No. 9,505,884, U.S. patent application Ser. No. 14/963,908 is a divisional of U.S. patent application Ser. No. 14/259,408 filed Apr. 23, 2014 and issued as U.S. Pat. No. 9,238,717, U.S. patent application Ser. No. 14/259,408 is a divisional of U.S. patent application Ser. No. 13/116,427 filed May 26, 2011 and issued as U.S. Pat. No. 8,742,063, U.S. patent application Ser. No. 13/116,427 claims the benefit of U.S. Provisional Application No. 61/349,469 entitled "Polymer Bonded Redox Molecules And Methods Of Making The Same" filed May 28, 2010, all of which are incorporated by reference in their entireties.

BACKGROUND

Biosensors usually analyze a sample of a biological fluid, such as whole blood, urine, or saliva. Samples are compositions that may contain an unknown amount of analyte. Typically, a sample is in liquid form and is an aqueous mixture. A sample may be a derivative of a biological sample, such as an extract, a dilution, a filtrate, or a reconstituted precipitate. A biosensor usually determines the concentration of one or more analytes, a substance present in the sample, such as ketones, glucose, uric acid, lactate, cholesterol, or bilirubin. An analysis determines the presence and/or concentration of the analyte in the sample. The analysis is useful in the diagnosis and treatment of physiological abnormalities. For example, a diabetic individual may use a biosensor to determine the glucose level in blood for adjustments to diet and/or medication.

A biological fluid may be obtained using a variety of methods. In one example of an invasive method, a lancet is used to pierce a user's skin to draw a biological fluid sample, such as blood. This sample is then analyzed with a biosensor external to the skin to determine the concentration of an analyte, such as glucose, in the sample. One disadvantage of this method is that the user's skin must be pierced each time an analyte concentration reading is desired.

One alternative to such an invasive method is to implant a biosensor under the user's skin. This method can allow for multiple analyte concentration readings to be obtained without making a new puncture in the skin for each reading. In addition, the analyte concentration may be monitored at regular intervals without any action required by the user. Thus, implantable biosensors may offer improvements in user compliance and in the amount of information provided.

Many biosensors measure an electrical signal to determine the analyte concentration in a sample of the biological fluid. The analyte typically undergoes an oxidation/reduction (redox) reaction when an excitation signal is applied to the sample. A redox reaction includes oxidation and reduction half-cells. The oxidation half-cell of the reaction involves the loss of at least one electron by the first species. The reduction half-cell involves the addition of at least one electron to the second species. The ionic charge of a species that is oxidized is made more positive by an amount equal to the number of electrons removed. Likewise, the ionic charge of a species that is reduced is made less positive by an amount equal to the number of electrons gained.

In electrochemical sensor systems, a test excitation signal initiates the redox reaction of the analyte in the sample of the biological fluid. The test excitation signal usually is an electrical signal, such as a current or potential, and may be constant, variable, or a combination thereof such as when an AC signal is applied with a DC signal offset. The test excitation signal may be applied as a single pulse or in multiple pulses, sequences, or cycles. The redox reaction generates a test output signal in response to the excitation signal. The output signal usually is another electrical signal, such as a current or potential, which may be measured and correlated with the concentration of the analyte in the sample. The output signal may be measured constantly or periodically during transient and/or steady-state output. Various electrochemical processes may be used such as amperometry, coulometry, voltammetry, gated amperometry, gated voltammetry, and the like.

An enzyme or similar species may be used to enhance the redox reaction of the analyte. The enzyme may be an analyte specific enzyme, such as glucose oxidase or glucose dehydrogenase, which catalyze the oxidation of glucose in a whole blood sample.

A mediator may be used to maintain the oxidation state of the enzyme. A mediator is a substance that may be oxidized or reduced and that may transfer one or more electrons. A mediator is a reagent and is not the analyte of interest, but provides for the indirect measurement of the analyte. More simply, the mediator undergoes a redox reaction in response to the oxidation or reduction of the analyte. The oxidized or reduced mediator then undergoes the opposite reaction at an electrode and is regenerated to its original oxidation number.

The mediator in an electrochemical biosensor may be a one electron transfer mediator or a multi-electron transfer mediator. One electron transfer mediators are chemical moieties capable of taking on one additional electron during the conditions of the electrochemical reaction. One electron transfer mediators include compounds, such as 1,1'-dimethyl ferrocene, ferrocyanide and ferricyanide, and ruthenium(III) and ruthenium(II) hexaamine. Multi-electron transfer mediators are chemical moieties capable of taking on more than one electron during the conditions of the reaction. Multi-electron transfer mediators include two electron transfer mediators, such as the organic quinones and hydroquinones, including phenanthroline quinone; phenothiazine and phenoxazine derivatives; 3-(phenylamino)-3H-phenoxazines; phenothiazines; and 7-hydroxy-9,9-dimethyl-9H-acridin-2-one and its derivatives. Two electron transfer mediators also include the electro-active organic molecules described in U.S. Pat. Nos. 5,393,615; 5,498,542; and 5,520,786.

Two electron mediators may have redox potentials that are at least 100 mV lower, more preferably at least 150 mV lower, than ferricyanide. Two electron transfer mediators include 3-phenylimino-3H-phenothiazines (PIPT) and 3-phenylimino-3H-phenoxazines (PIPO). Two electron mediators also include the carboxylic acid or salt, such as ammonium salts, of phenothiazine derivatives. Two electron mediators further include (E)-2-(3H-phenothiazine-3-ylideneamino)benzene-1,4-disulfonic acid (Structure A), (E)-5-(3H-phenothiazine-3-ylideneamino)isophthalic acid (Structure B), ammonium (E)-3-(3H-phenothiazine-3-ylideneamino)-5-carboxybenzoate (Structure C), and combinations thereof. The structural formulas of these mediators are presented below. While only the di-acid form of the Structure A mediator is shown, mono- and di-alkali metal salts of the acid are included. The sodium salt of the acid may be used for the Structure A mediator. Alkali-metal salts of the Structure B mediator also may be used.

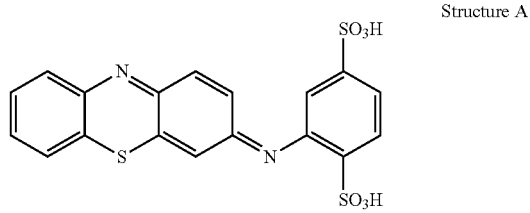

Structure A

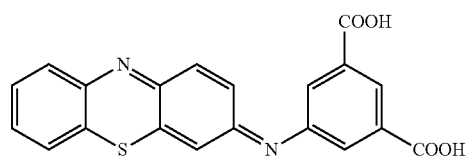

Structure B

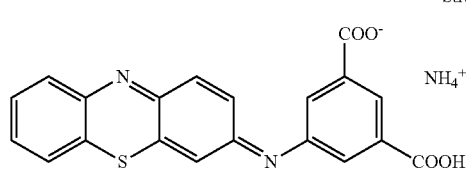

Structure C

One drawback to the use of implantable electrochemical biosensors is that one or more of the reagents of the biosensor may be released into the biological sample during the analysis. Thus, one or more of the reagents, such as a mediator, may leach from the biosensor into the bodily fluid of the user. Leaching of reagents from the biosensor over time can result in decreased accuracy of the readings obtained from the biosensor. In addition, the reagents may cause undesirable physiological effects if they are released into the patient at a level or rate that is too large.

Mediators bonded to polymers have been investigated as possible non-leaching mediators in electrochemical biosensors; however, these systems have met with mixed success. Polymer bonded mediators may have insufficient reactivity in a redox reaction in response to the oxidation or reduction of the analyte. Some polymer bonded mediators include transition metals, which could be harmful if released into the bodily fluid of the user.

Accordingly, it would be desirable to have reagents for electrochemical biosensors that do not substantially leach into the biological fluid of the patient. Preferably such non-leaching mediators would be effective in transferring electrons between the analyte and the electrodes and/or in maintaining the oxidation state of the enzyme.

SUMMARY

In one aspect, the invention provides a polymer that includes a polymeric backbone and a plurality of phenothiazine groups bonded to the polymeric backbone. The plurality of phenothiazine groups includes at least one of a phenothiazine group having the general formula (IV):

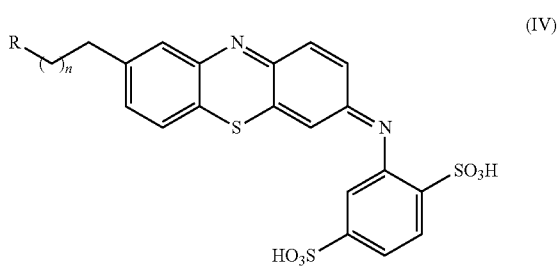

(IV)

and salts thereof, where n is about 9 and "R" represents the polymeric backbone to which the phenothiazine group is bonded, and a phenothiazine group having the general formula (V):

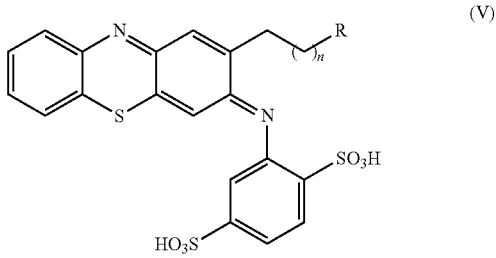

(V)

and salts thereof, where n is about 9 and "R" represents the polymeric backbone to which the phenothiazine group is bonded.

In another aspect, the invention provides a method of making the above polymer. The method includes forming the polymer from a polymer having a precursor polymeric backbone and a plurality of nucleophilic side groups bonded to the precursor polymeric backbone, and a mixture of 2-(8-(ω-haloalkyl)-3H-phenothiazin-3-ylideneamino)benzene-1,4-disulfonic acid and 2-(2-(ω-haloalkyl)-3H-phenothiazin-3-ylideneamino)benzene-1,4-disulfonic acid.

In another aspect, the invention provides a method of making the above polymer. The method includes forming the polymer from a compound having a plurality of epoxide groups, and a mixture of 2-(8-(ω-(bis(ω-hydroxyalkyl)amino)alkyl)-3H-phenothiazin-3-ylideneamino)benzene-1,4-disulfonic acid and 2-(2-(ω-(bis(ω-hydroxyalkyl)amino)alkyl)-3H-phenothiazin-3-ylideneamino)benzene-1,4-disulfonic acid.

In another aspect, the invention provides a polymer having the general formula (VI):

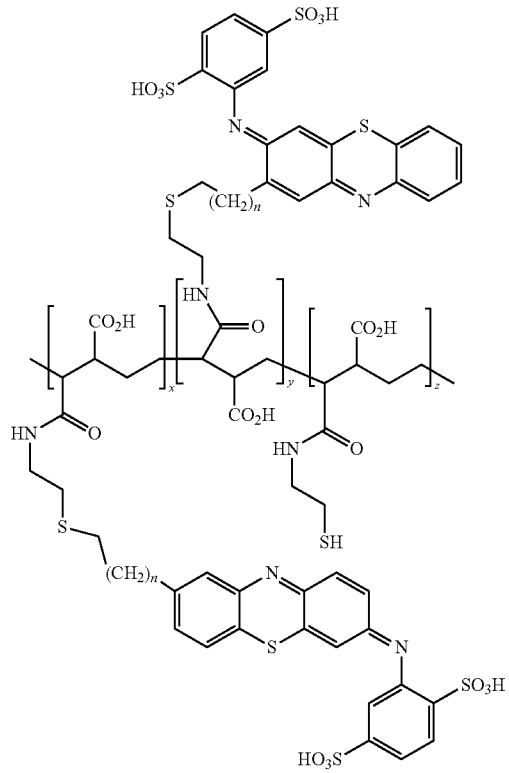

and salts thereof; where n is about 9, x and y independently are an integer from 1 to 100,000, and z is an integer from 0 to 100,000.

In another aspect, the invention provides a method of making the above polymer. The method includes forming the polymer from poly(β-carboxyl-γ-(2-mercaptoethyl)carbamoyl-butene), and a mixture of 2-(8-(ω-haloalkyl)-3H-phenothiazin-3-ylideneamino)benzene-1,4-disulfonic acid and 2-(2-(ω-haloalkyl)-3H-phenothiazin-3-ylideneamino)benzene-1,4-disulfonic acid.

In another aspect, the invention provides a polymer having the general formula (VII):

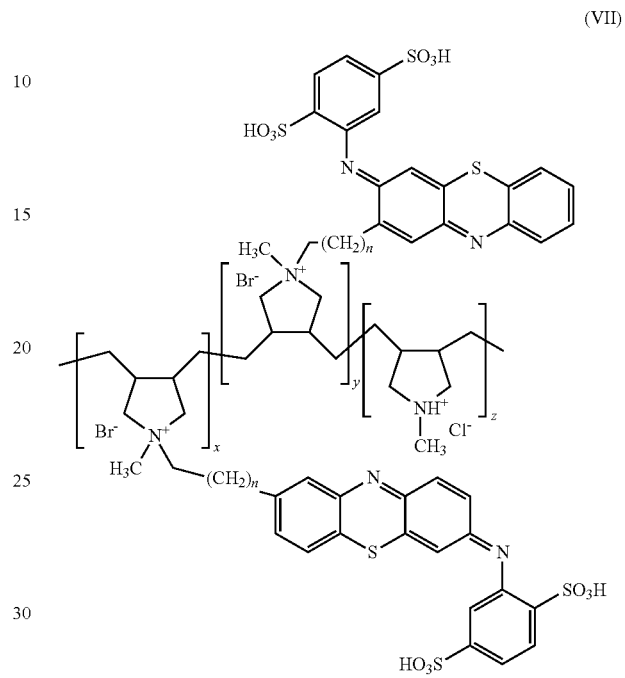

and salts thereof; where n is about 9, x and y independently are an integer from 1 to 10,000, and z is an integer from 0 to 10,000.

In another aspect, the invention provides a method of making the above polymer. The method includes forming the polymer from poly(diallylmethylamine), and a mixture of 2-(8-(ω-haloalkyl)-3H-phenothiazin-3-ylideneamino)benzene-1,4-disulfonic acid and 2-(2-(ω-haloalkyl)-3H-phenothiazin-3-ylideneamino)benzene-1,4-disulfonic acid.

In another aspect, the invention provides a polymer having the general formula (VIII):

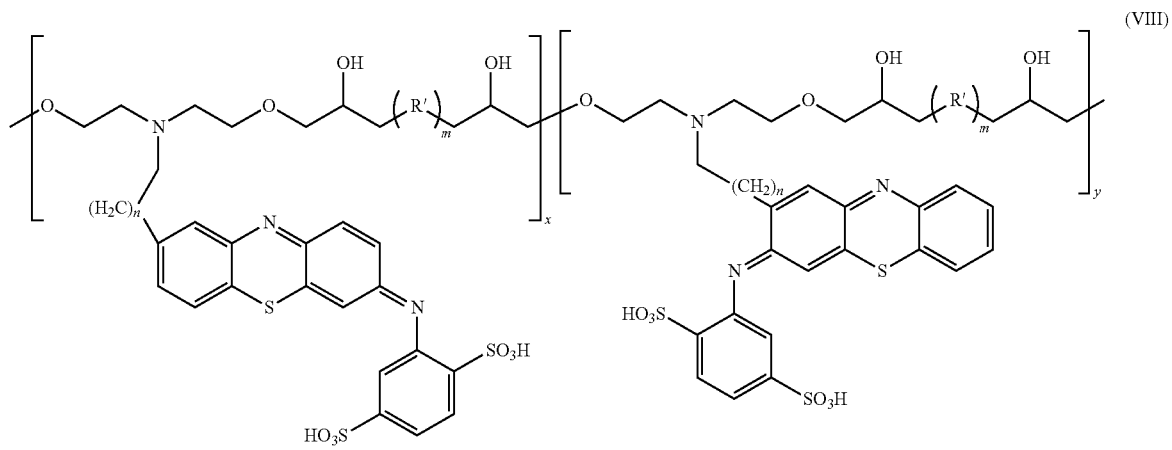

and salts thereof, where R' is an organic group, where m is 0 or 1, where n is about 9, and where x and y independently are an integer from 1 to 10,000.

In another aspect, the invention provides a method of making the above polymer. The method includes forming the polymer from a diepoxyalkane, and a mixture of 2-(8-(ω-(bis(ω-hydroxyalkyl)amino)alkyl)-3H-phenothiazin-3-ylideneamino)benzene-1,4-disulfonic acid and 2-(2-(ω-(bis(ω-hydroxyalkyl)amino)alkyl)-3H-phenothiazin-3-ylideneamino)benzene-1,4-disulfonic acid.

The scope of the present invention is defined solely by the appended claims and is not affected by the statements within this summary.

BRIEF DESCRIPTION OF THE DRAWINGS

The invention can be better understood with reference to the following drawings and description. The components in the figures are not necessarily to scale and are not intended to accurately represent molecules or their interactions, emphasis instead being placed upon illustrating the principles of the invention. Moreover, in the figures, like referenced numerals designate corresponding parts throughout the different views.

DETAILED DESCRIPTION

A non-leaching mediator includes a compound or a mixture of compounds that is not substantially released into a biological sample, but that may be oxidized or reduced, and may transfer one or more electrons from the sample to an electrode of a biosensor. A non-leaching mediator also includes a polymer having a polymeric backbone and a plurality of functional groups bonded to the polymeric backbone, where the functional groups may be oxidized or reduced, and may transfer one or more electrons from the sample to an electrode of a biosensor.

The non-leaching mediator has sufficient solubility in the sample to provide for the indirect measurement of the analyte, undergoing a redox reaction in response to the oxidation or reduction of the analyte. The oxidized or reduced mediator responsive to the analyte concentration of the sample then undergoes the opposite redox reaction at the working electrode of the biosensor and is regenerated to its original oxidation number. A measuring device may correlate the electrons flowing through the working electrode with the analyte concentration of the sample.

A non-leaching mediator may have sufficient solubility to provide for the indirect measurement of the analyte, even if the entire mediator does not dissolve fully in the sample. For example, a non-leaching mediator may include a functional group that may be oxidized or reduced, and this functional group may be solubilized by the sample while at least a portion of the remainder of the mediator is not solubilized in the sample.

A non-leaching mediator compound may have the general formula (I):

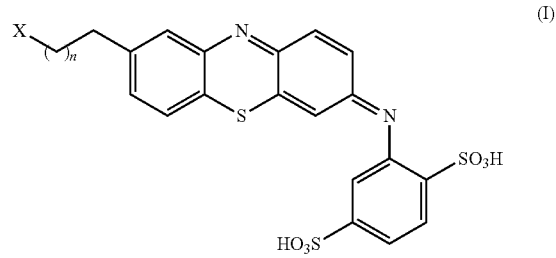

and salts thereof, where n is about 9, X is a halogen, and X is preferably bromine.

The term "salts thereof" means a compound in which the —H atoms of one or both of the —SO$_3$H groups is replaced with a cation independently selected from the group consisting of alkali metal ions, alkaline earth metal ions and ammonium ions. The term "halogen" means —F, —Cl, —Br or —I.

A non-leaching mediator compound may have the general formula (II):

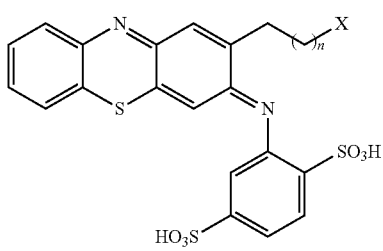

and salts thereof, where n is about 9, X is a halogen, and X is preferably bromine.

A non-leaching mediator composition may include a mixture of a first compound having the general formula (I) and salts thereof, and a second compound having the general formula (II) and salts thereof, where X is preferably bromine.

Figure 1A:
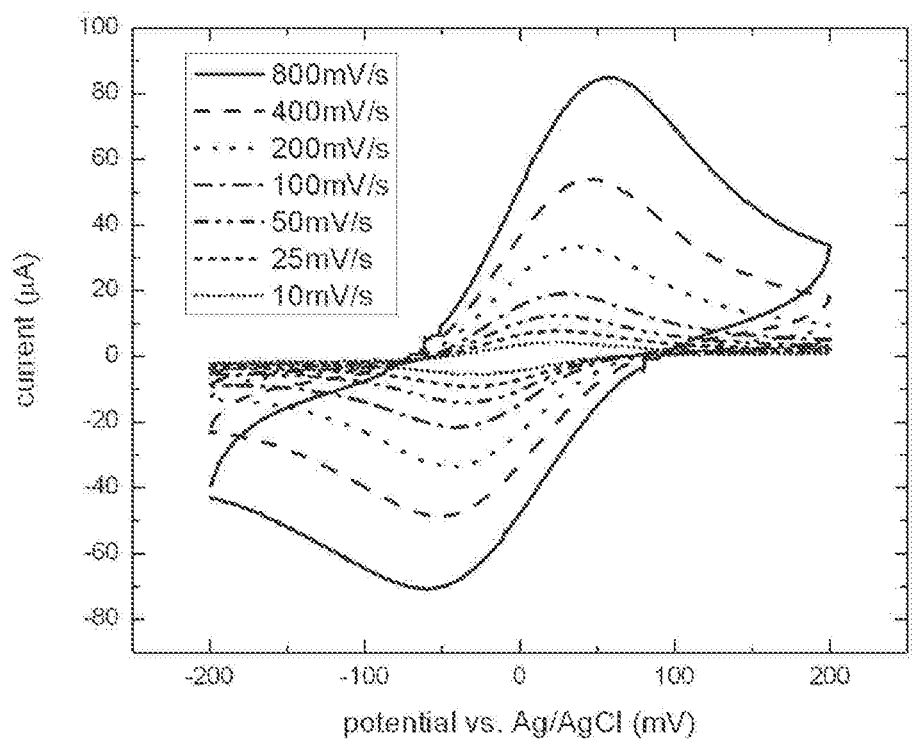
FIGS. 1A and 1B depict graphs illustrating output currents from mediator reduction in response to an input potential.
Figure 1B:
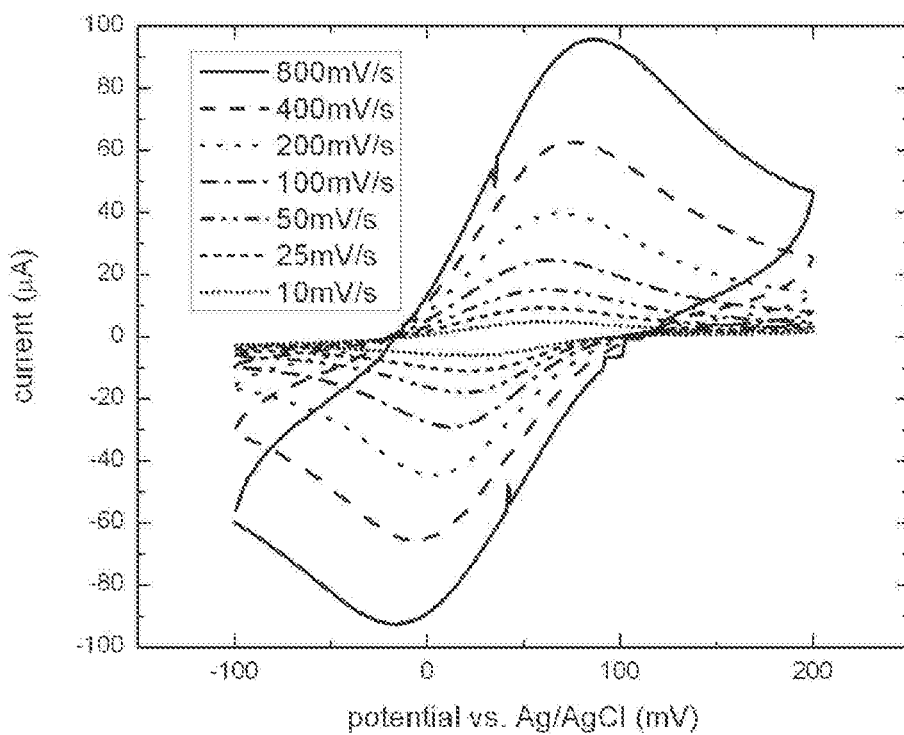

FIGS. 1A and 1B depict graphs illustrating output currents from mediator reduction in response to an input potential. The mediator was a composition including a 3:2 molar mixture of a first compound having the general formula (I), and a second compound having the general formula (II), where X is bromine and each compound is present as the disodium salt. A 5 mm glassy carbon electrode served as a working electrode (WE), Ag/AgCl as a reference electrode (RE), and platinum gauze as a counter electrode (CE). In FIG. 1A, the mediator composition was present at a concentration of 1 mg/mL in a mixture containing 10 mM PBS buffer (pH 7.4), and the input potential was scanned between −200 mV and 200 mV vs. Ag/AgCl. In FIG. 1B, the mediator composition was present at a concentration of 1 mg/mL in a mixture containing 100 mM PBS (pH 7.0) and 100 mM NaCl buffer solution, and the input potential was scanned between −100 mV and 200 mV vs. Ag/AgCl. The rate of change of the input potential was varied from 10 mV/s to 800 mV/s, as indicated in FIGS. 1A and 1B. Referring to FIG. 1B, when the scan rate was less than 50 mV/s, the oxidative and reductive peak separation was around 30-40 mV. This separation indicates that the reduction of this composition was a two-electron process, which is close to the theoretical limit of Nernstian behavior at 60 mV/2e.

The redox potential of the mediator composition of FIGS. 1A and 1B was about −3 mV vs. Ag/AgCl in the 10 mM PBS buffer (pH 7.4), and was about 40 mV vs. Ag/AgCl in the mixture of 100 mM PBS (pH 7.0) and 100 mM NaCl buffer. These redox potentials are similar to that of the conventional mediator (E)-2-(3H-phenothiazine-3-ylideneamino)benzene-1,4-disulfonic acid (Structure A), which is −50 mV vs. Ag/AgCl.

The open circuit voltage between the WE and the RE also was measured for the mediator composition of FIGS. 1A and 1B. The open circuit voltage is a measure of the redox state of the mediator. The open circuit voltage of the mixture was 59 mV vs. Ag/AgCl in the 10 mM PBS buffer, which suggests that the mediator was in its oxidized state after synthesis.

Figure 2:
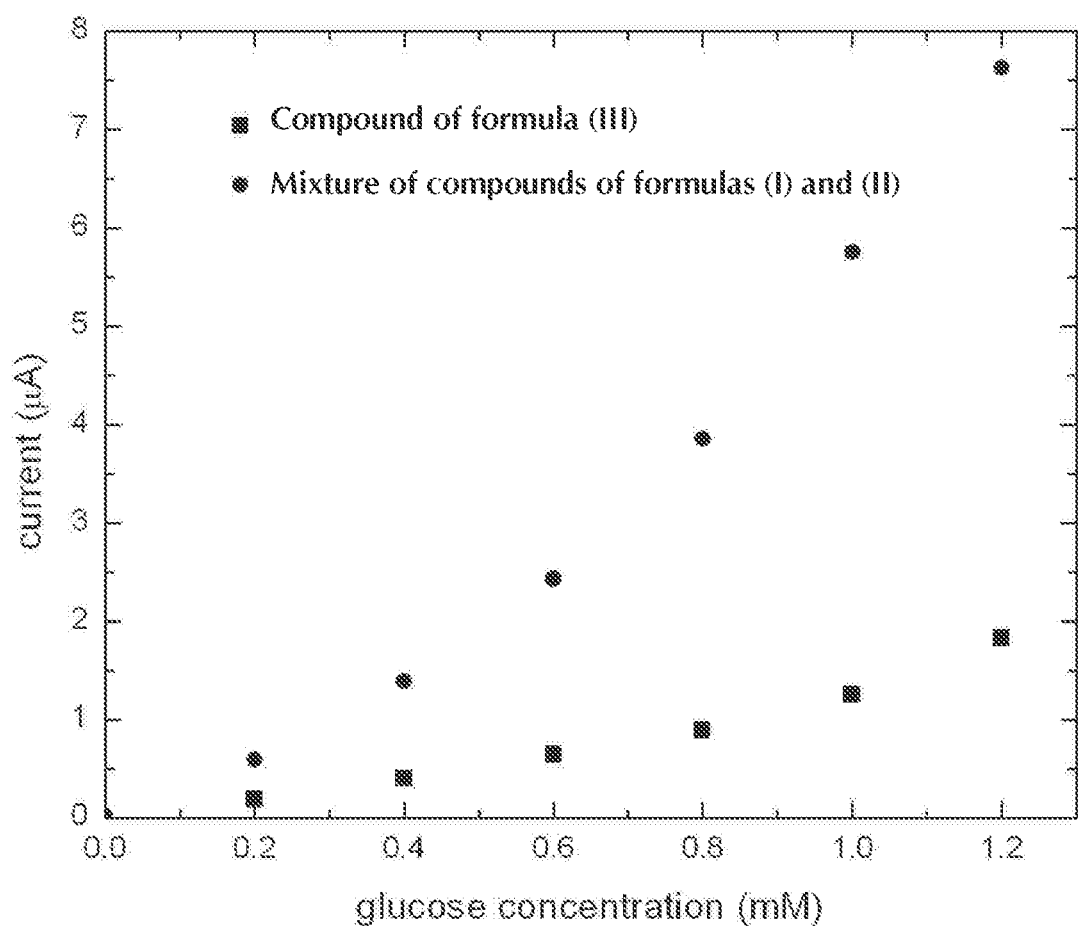
FIG. 2 depicts a graph illustrating output currents from mediator reduction in response to an input potential when the mediator is in a mixture containing glucose and glucose dehydrogenase.

FIG. 2 depicts a graph illustrating output currents from mediator oxidation in response to an input potential when the mediator is in a mixture containing glucose and glucose dehydrogenase. The mediator was the composition used in FIGS. 1A and 1B. A 5 mm glassy carbon electrode served as a WE, Ag/AgCl as a RE, and platinum gauze as a CE. The composition was present at a concentration of 2 mg/mL in a mixture containing 10 mM PBS buffer (pH 7.4), and the input potential was 100 mV vs. Ag/AgCl. The output current increased as the glucose concentration increased from 0 to 1.2 mM in the mixture. Thus, the composition may be used as a mediator for the redox reaction correlating the glucose concentration in a sample with an electrical signal.

Figure 3:
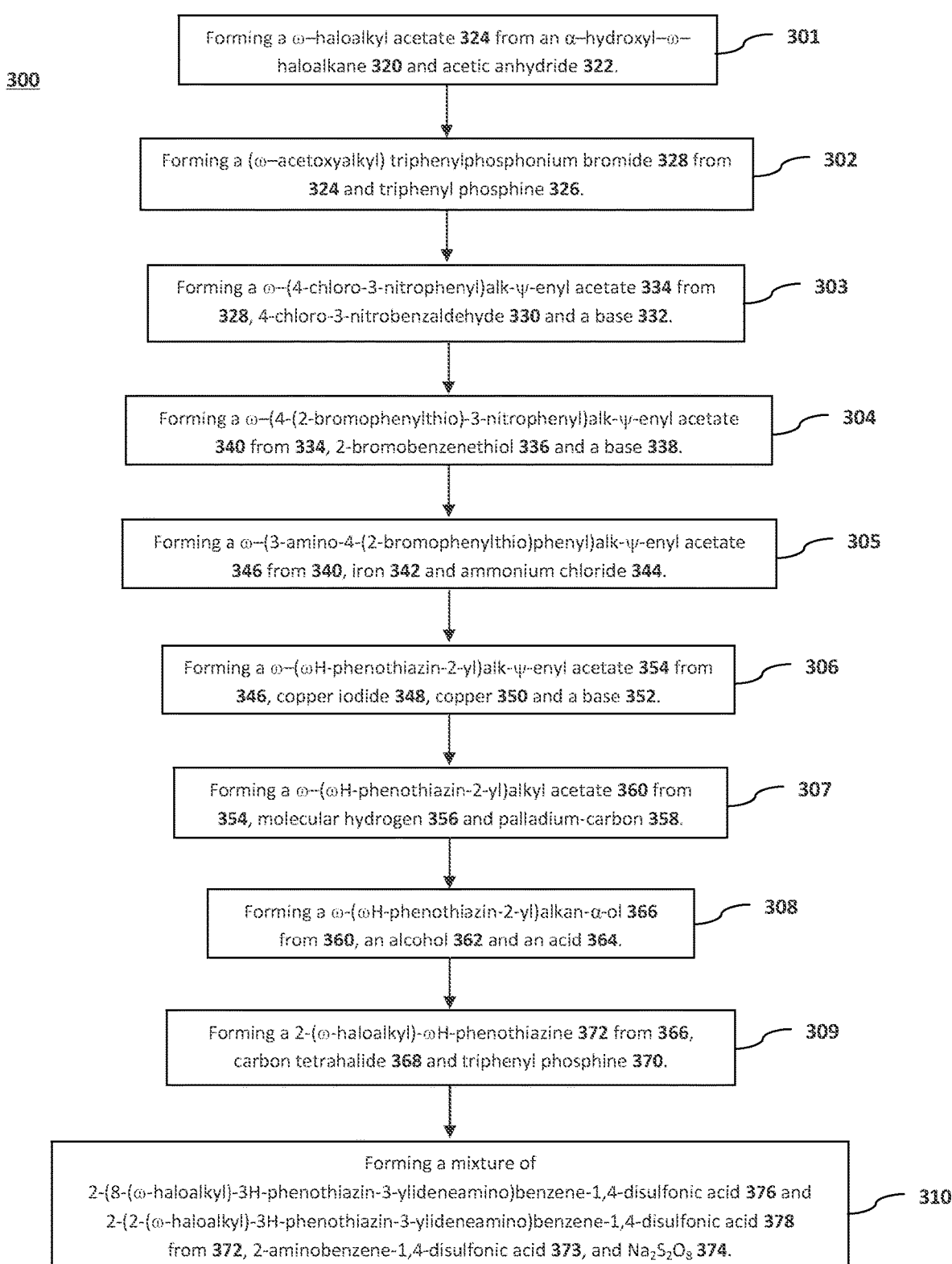
FIG. 3 depicts a method for making a composition including at least one compound having the general formula (I) or (II).

FIG. 3 depicts a method 300 of making a composition including at least one compound having the general formula (I) or (II) and salts thereof. The method 300 includes forming 301 a ω-haloalkyl acetate 324 from an α-hydroxyl-ω-haloalkane 320 and acetic anhydride 322; forming 302 a (ω-acetoxyalkyl) triphenylphosphonium bromide 328 from the ω-haloalkyl acetate 324 and triphenyl phosphine 326; forming 303 a ω-(4-chloro-3-nitrophenyl)alk-ψ-enyl acetate 334 from the (ω-acetoxyalkyl) triphenylphosphonium bromide 328, 4-chloro-3-nitrobenzaldehyde 330 and a base 332; forming 304 a ω-(4-(2-bromophenylthio)-3-nitrophenyl)alk-ψ-enyl acetate 340 from the ω-(4-chloro-3-nitrophenyl) alk-ψ-enyl acetate 334, 2-bromobenzenethiol 336 and a base 338; forming 305 a ω-(3-amino-4-(2-bromophenylthio)phenyl)alk-ψ-enyl acetate 346 from the ω-(4-(2-bromophenylthio)-3-nitrophenyl)alk-ψ-enyl acetate 340, iron 342 and ammonium chloride 344; forming 306 a ω-(ωH-phenothiazin-2-yl)alk-ψ-enyl acetate 354 from the ω-(3-amino-4-(2-bromophenylthio)phenyl)alk-ψ-enyl acetate 346, copper iodide 348, copper 350 and a base 352; forming 307 a ω-(ωH-phenothiazin-2-yl)alkyl acetate 360 from the ω-(ωH-phenothiazin-2-yl)alk-ψ-enyl acetate 354, molecular hydrogen 356 and palladium-carbon 358; forming 308 a ω-(ωH-phenothiazin-2-yl)alkan-α-ol 366 from the ω-(ωH-phenothiazin-2-yl)alkyl acetate 360, an alcohol 362 and an acid 364; forming 309 a 2-(ω-haloalkyl)-ωH-phenothiazine 372 from the ω-(ωH-phenothiazin-2-yl)alkan-α-ol 366, carbon tetrahalide 368 and triphenyl phosphine 370; and forming 310 a mixture of 2-(8-(ω-haloalkyl)-3H-phenothiazin-3-ylideneamino)benzene-1,4-disulfonic acid 376 and 2-(2-(ω-haloalkyl)-3H-phenothiazin-3-ylideneamino) benzene-1,4-disulfonic acid 378 from the 2-(ω-haloalkyl)-ωH-phenothiazine 372, 2-aminobenzene-1,4-disulfonic acid 373 and $Na_2S_2O_8$ 374. Products 376 and 378 are examples of compounds having the general formula (I) and (II), respectively.

Figure 4:
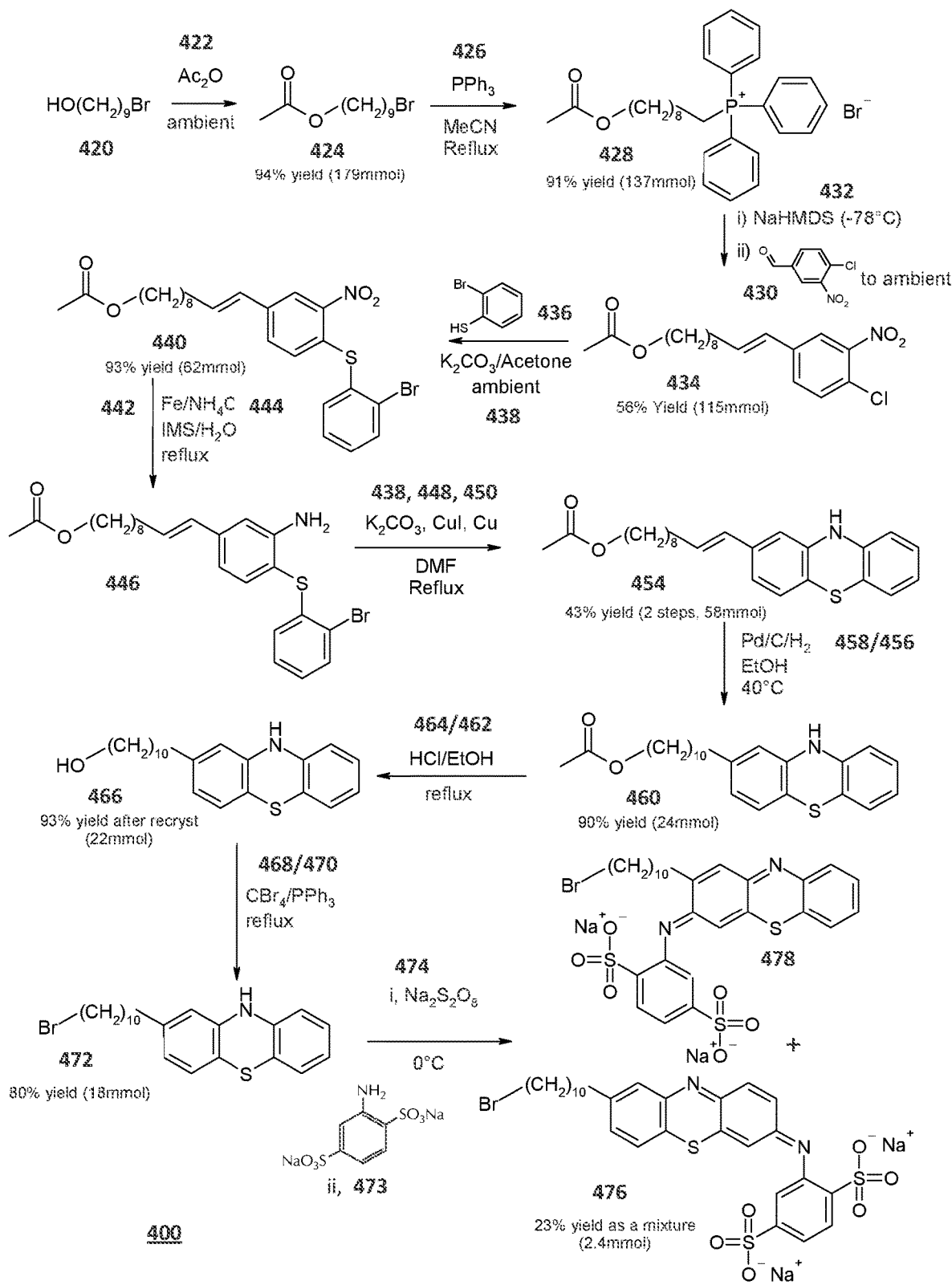
FIG. 4 depicts chemical structures, reaction schemes and product yields for a method of making a composition including a mixture of a first compound having the general formula (I), and a second compound having the general formula (II), where X is bromine and each compound is present as the disodium salt.

FIG. 4 depicts chemical structures, reaction schemes and product yields for a method 400 of making a composition including a mixture of a first compound having the general formula (I), and a second compound having the general formula (II), where X is bromine and each compound is present as the disodium salt. Method 400 includes forming 9-bromononyl acetate 424 from 9-halononan-1-ol 420 and acetic anhydride 422; forming (9-acetoxynonyl)triphenylphosphonium 428 from 9-bromononyl acetate 424 and triphenyl phosphine 426; forming 10-(4-chloro-3-nitrophenyl) dec-9-enyl acetate 434 from (9-acetoxynonyl) triphenylphosphonium 428, 4-chloro-3-nitrobenzaldehyde 430 and sodium bis(trimethylsilyl)amide (NaHMDS) 432; forming 10-(4-(2-bromophenylthio)-3-nitrophenyl)dec-9-enyl acetate 440 from 10-(4-chloro-3-nitrophenyl)dec-9-enyl acetate 434, 2-bromobenzenethiol 436 and $K_2CO_3$ 438; forming 10-(3-amino-4-(2-bromophenylthio)phenyl)dec-9-enyl acetate 446 from 10-(4-(2-bromophenylthio)-3-nitrophenyl)dec-9-enyl acetate 440, iron 442 and ammonium chloride 444; forming 10-(10H-phenothiazin-2-yl)dec-9-enyl acetate 454 from 10-(3-amino-4-(2-bromophenylthio) phenyl)dec-9-enyl acetate 446, copper iodide 448, copper

450 and $K_2CO_3$ 438; forming 10-(10H-phenothiazin-2-yl)decyl acetate 460 from 10-(10H-phenothiazin-2-yl)dec-9-enyl acetate 454, molecular hydrogen 456 and palladium-carbon 458; forming 10-(10H-phenothiazin-2-yl)decan-1-ol 466 from 10-(10H-phenothiazin-2-yl)decyl acetate 460, ethanol 462 and HCl 464; forming 2-(10-bromodecyl)-10H-phenothiazine 472 from 10-(10H-phenothiazin-2-yl)decan-1-ol 466, carbon tetrabromide 468 and triphenyl phosphine 470; and forming a mixture of 2-(8-(10-bromodecyl)-3H-phenothiazin-3-ylideneamino)benzene-1,4-disulfonic acid 476 and 2-(2-(10-bromodecyl)-3H-phenothiazin-3-ylideneamino)benzene-1,4-disulfonic acid 478 from the 2-(10-bromodecyl)-10H-phenothiazine 472, 2-aminobenzene-1,4-disulfonic acid 473 and $Na_2S_2O_8$ 474. Products 476 and 478 are examples of compounds having the general formula (I) and (II), respectively.

A non-leaching mediator compound may have the general formula (III):

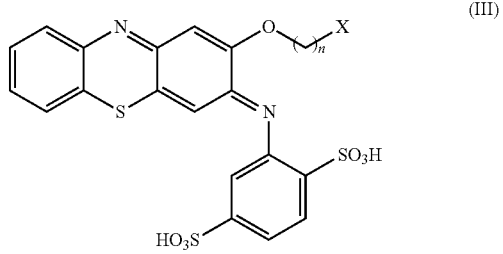

(III)

and salts thereof, where n is about 8, X is a halogen, and X is preferably bromine.

Figure 5A:
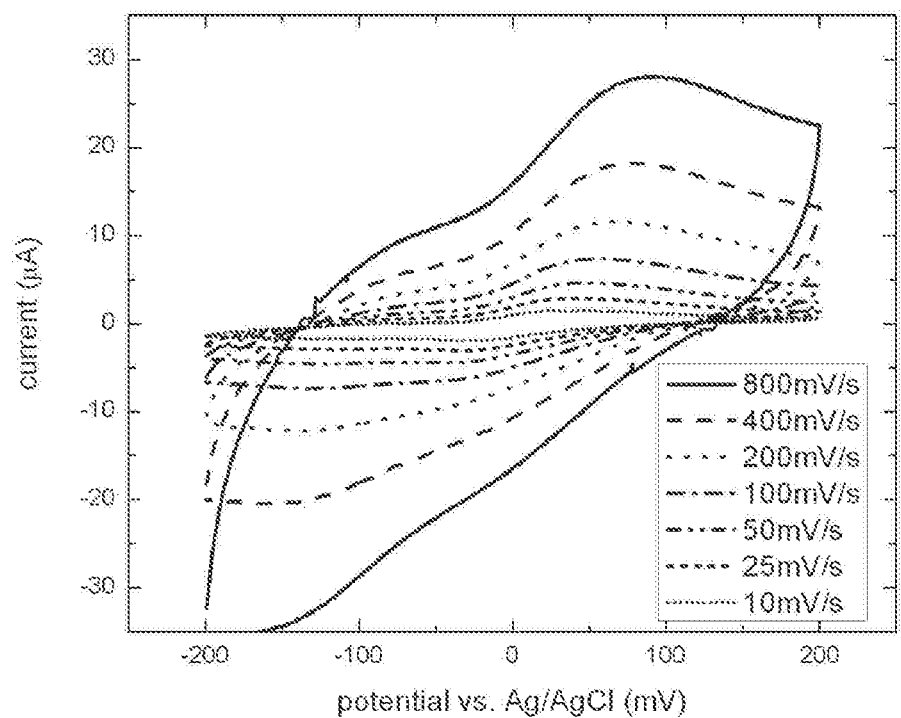
FIGS. 5A and 5B depict graphs illustrating output currents from mediator reduction in response to an input potential.
Figure 5B:
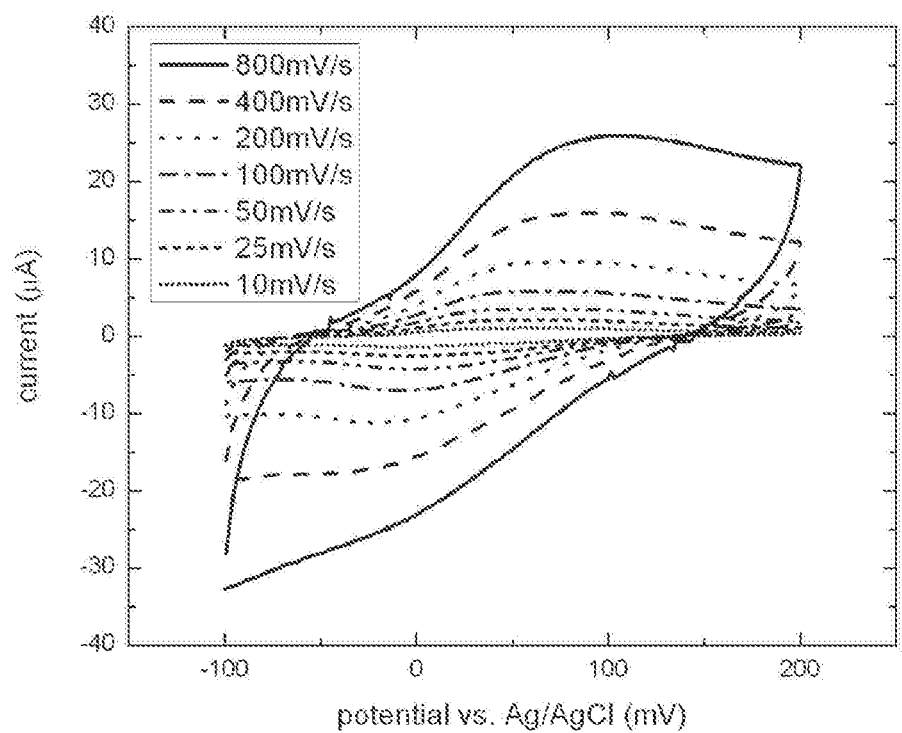

FIG. 5A and FIG. 5B depict graphs illustrating output currents from mediator reduction in response to an input potential. The mediator was a compound having general formula (III), where X is bromine. A 5 mm glassy carbon electrode served as a WE, Ag/AgCl as a RE, and platinum gauze as a CE. In FIG. 5A, the mediator was present at a concentration of 1 mg/mL in a mixture containing 10 mM PBS buffer (pH 7.4), and the input potential was scanned between −200 mV and 200 mV vs. Ag/AgCl. In FIG. 5B, the mediator was present at a concentration of 1 mg/mL in a mixture containing 100 mM PBS (pH 7.0) and 100 mM NaCl buffer solution, and the input potential was scanned between −100 mV and 200 mV vs. Ag/AgCl. The rate of change of the input potential was varied from 10 mV/s to 800 mV/s, as indicated in FIGS. 5A and 5B. Referring to FIG. 5B, when the scan rate was less than 50 mV/s, the oxidative and reductive peak separation was around 30-40 mV. This separation indicates that the reduction of this mediator was a two-electron process, which is close to the theoretical limit of Nernstian behavior at 60 mV/2e.

The redox potential of the compound having general formula (III), where X is bromine, was about 3 mV vs. Ag/AgCl in the 10 mM PBS buffer (pH 7.4), and was about 15 mV vs. Ag/AgCl in the mixture of 100 mM PBS (pH 7.0) and 100 mM NaCl buffer. These redox potentials are similar to that of the conventional mediator (E)-2-(3H-phenothiazine-3-ylideneamino)benzene-1,4-disulfonic acid (Structure A), which is −50 mV vs. Ag/AgCl.

The open circuit voltage between the WE and the RE also was measured for the compound having general formula (III), where X is bromine. The open circuit voltage of the compound was 111 mV vs. Ag/AgCl in the 10 mM PBS buffer, which suggests that the mediator was in its oxidized state after synthesis.

Referring to FIG. 2, a compound having general formula (III), where X is bromine, can be used as a mediator for the redox reaction correlating the glucose concentration of a sample with an electrical signal. A 5 mm glassy carbon electrode served as a WE, Ag/AgCl as a RE, and platinum gauze as a CE. The mediator was present at a concentration of 3 mg/mL in a mixture containing 10 mM PBS buffer (pH 7.4), and the input potential was 100 mV vs. Ag/AgCl. The output current increased as the glucose concentration increased from 0 to 1.2 mM in the mixture. Thus, the composition may be used as a mediator for the redox reaction correlating the glucose concentration in a sample with an electrical signal.

Figure 6:
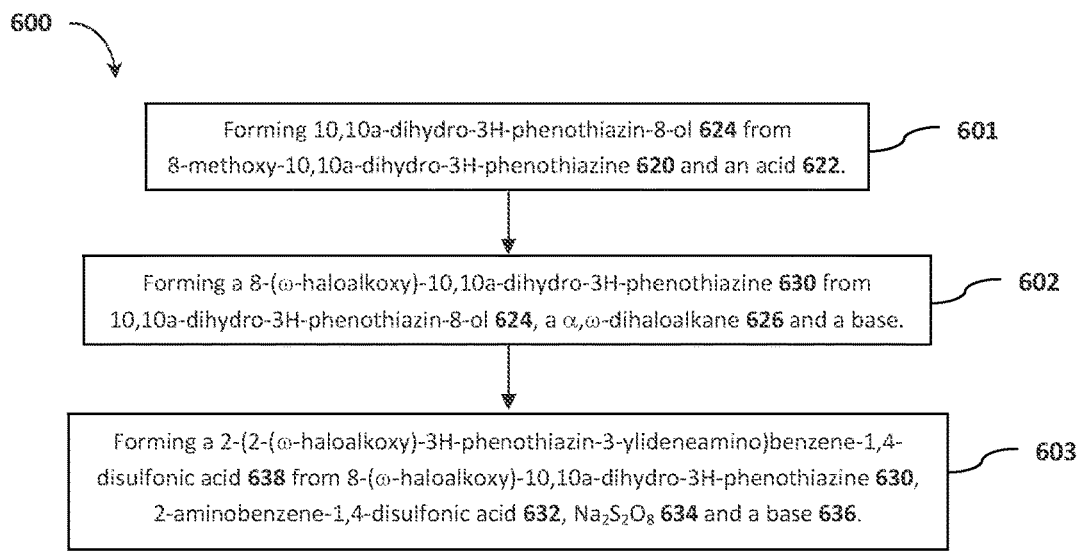
FIG. 6 depicts a method for making a compound having the general formula (III).

FIG. 6 depicts a method 600 of making a compound having the general formula (III) and salts thereof. The method 600 includes forming 601 10,10a-dihydro-3H-phenothiazin-8-ol 624 from 8-methoxy-10,10a-dihydro-3H-phenothiazine 620 and an acid 622; forming 602 a 8-(ω-haloalkoxy)-10,10a-dihydro-3H-phenothiazine 630 from 10,10a-dihydro-3H-phenothiazin-8-ol 624, a α,ω-dihaloalkane 626 and a base 628; and forming 603 a 2-(2-(ω-haloalkoxy)-3H-phenothiazin-3-ylideneamino)benzene-1,4-disulfonic acid 638 from 8-(ω-haloalkoxy)-10,10a-dihydro-3H-phenothiazine 630, 2-aminobenzene-1,4-disulfonic acid 632, $Na_2S_2O_8$ 634 and a base 636. Product 638 is an example of a compound having the general formula (III).

Figure 7:
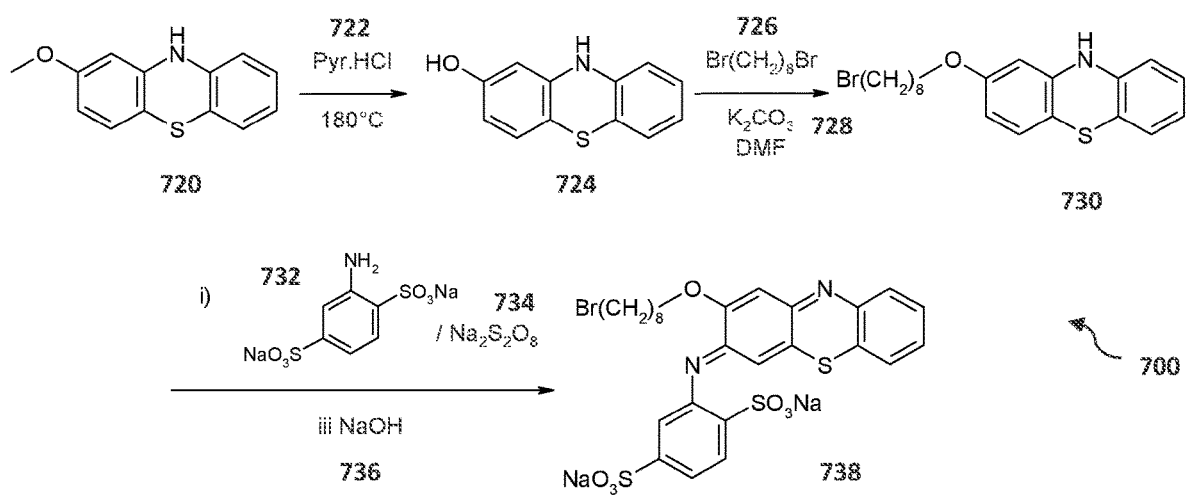
FIG. 7 depicts chemical structures and reaction schemes for a method of making a compound having the general formula (III), where X is bromine and the compound is present as the disodium salt.

FIG. 7 depicts chemical structures and reaction schemes for an example of a method 700 of making a compound having the general formula (III), where X is bromine and the compound is present as the disodium salt. Method 700 includes forming 10,10a-dihydro-3H-phenothiazin-8-ol 724 from 8-methoxy-10,10a-dihydro-3H-phenothiazine 720 and HCl 722; forming 8-(8-bromooctanoxy)-10,10a-dihydro-3H-phenothiazine 730 from 10,10a-dihydro-3H-phenothiazin-8-ol 724, 1,8-dibromooctane 726 and potassium carbonate 728; and forming 2-(2-(8-bromooctanoxy)-3H-phenothiazin-3-ylideneamino)benzene-1,4-disulfonic acid 738 from 8-(8-bromooctanoxy)-10,10a-dihydro-3H-phenothiazine 730, 2-aminobenzene-1,4-disulfonic acid 732, $Na_2S_2O_8$ 734 and sodium hydroxide 736. Product 738 is an example of a compound having the general formula (III).

A non-leaching mediator polymer may include a polymeric backbone and a plurality of functional groups bonded to the polymeric backbone, where the functional groups may be oxidized or reduced. In one example, the plurality of functional groups may include a plurality of phenothiazine groups bonded to the polymeric backbone. A phenothiazine group bonded to a polymeric backbone may include at least one of a phenothiazine group having the general formula (IV):

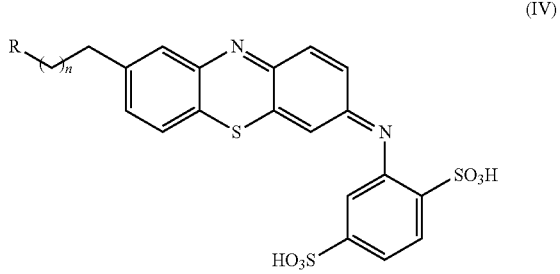

(IV)

and salts thereof, where n is about 9 and "R" represents the polymeric backbone to which the phenothiazine group is bonded, and a phenothiazine group having the general formula (V):

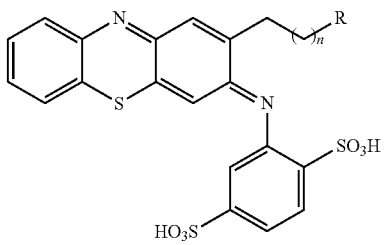

and salts thereof, where n is about 9 and "R" represents the polymeric backbone to which the phenothiazine group is bonded.

Preferably the plurality of functional groups are bonded to the polymeric backbone through carbon-heteroatom bonds. If the plurality of functional groups includes a phenothiazine group having formula (IV) or (V), the phenothiazine group preferably is bonded to the polymeric backbone through an ether group, an ester group, a carbonate group, a urea group, a urethane group, an amine group, an amide group, a thioether group, a thiourea group or a sulfonamide group.

A non-leaching mediator polymer that includes a polymeric backbone and a plurality of functional groups bonded to the polymeric backbone, where the functional groups may be oxidized or reduced, may include a polymer having the general formula (VI):

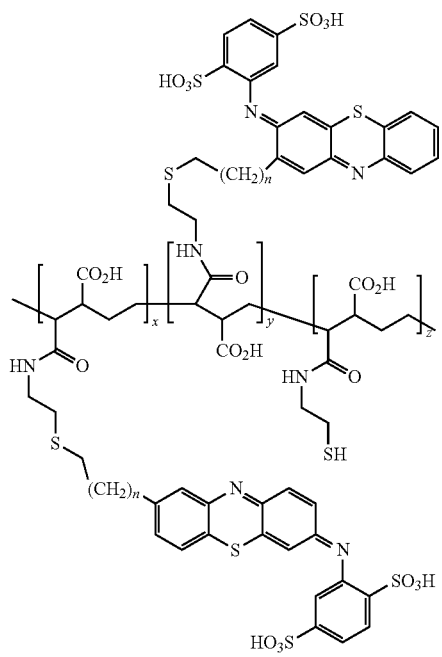

and salts thereof, where n is about 9, where x and y independently are an integer from 1 to 100,000, and where z is an integer from 0 to 100,000.

Preferably, the sum of x, y, and z in the polymer having the general formula (VI) is from 100 to 100,000. More preferably the sum of x, y, and z is from 500 to 10,000. Preferably x and y independently are an integer from 10 to 2,000. More preferably x and y independently are an integer from 20 to 1,000, and more preferably are an integer from 40 to 500. Preferably the mole fraction of x and y is from 0.05 to 0.9, where the mole fraction of x and y is calculated as (x+y)/(x+y+z). More preferably the mole fraction of x and y is from 0.07 to 0.7, and more preferably is from 0.1 to 0.5.

A non-leaching mediator polymer that includes a polymeric backbone and a plurality of functional groups bonded to the polymeric backbone, where the functional groups may be oxidized or reduced, may include a polymer having the general formula (VII):

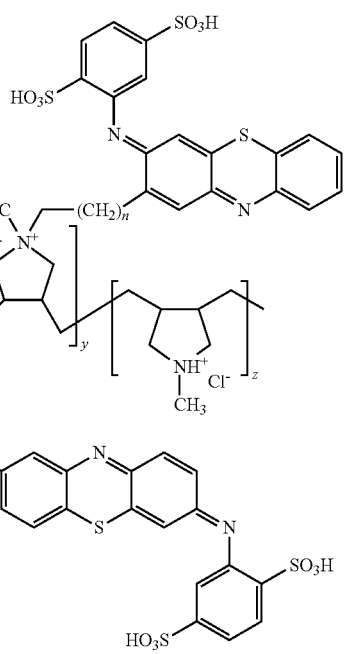

and salts thereof, where n is about 9, where x and y independently are an integer from 1 to 10,000, and where z is an integer from 0 to 10,000.

Preferably, the sum of x, y, and z in the polymer having the general formula (VI) is from 10 to 10,000. More preferably the sum of x, y, and z is from 20 to 1,000. Preferably x and y independently are an integer from 1 to 70. More preferably x and y independently are an integer from 2 to 20, and more preferably are an integer from 30 to 10. Preferably the mole fraction of x and y is from 0.05 to 0.9. More preferably the mole fraction of x and y is from 0.07 to 0.7, and more preferably is from 0.1 to 0.5.

Figure 8A:
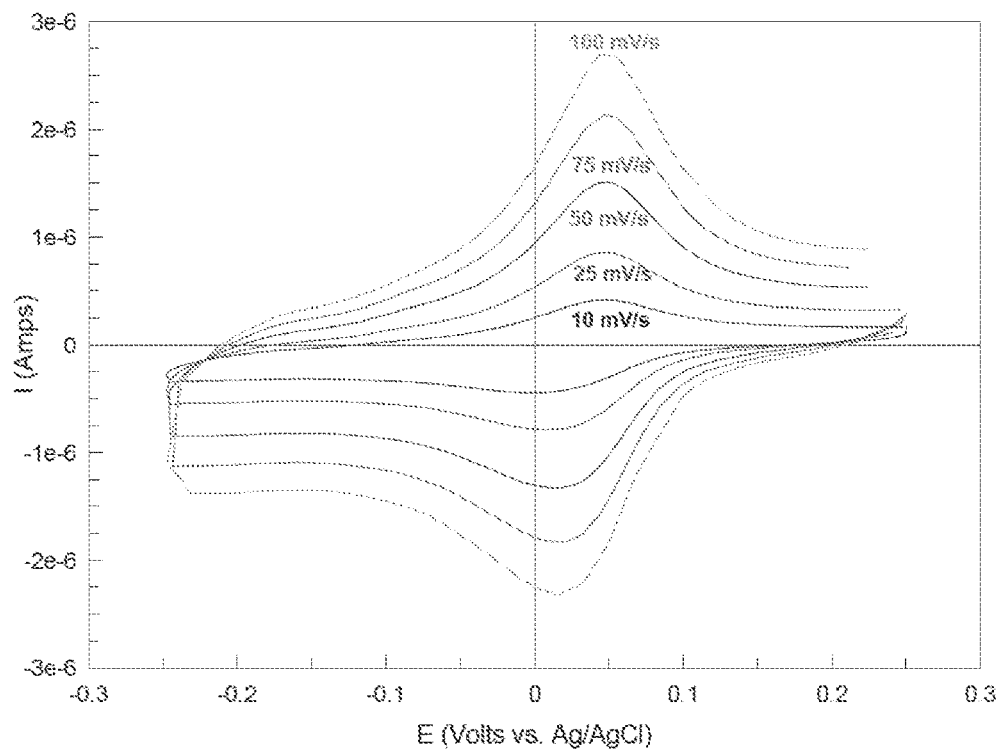
FIGS. 8A and 8B depict graphs illustrating output currents from mediator reduction in response to an input potential.
Figure 8B:
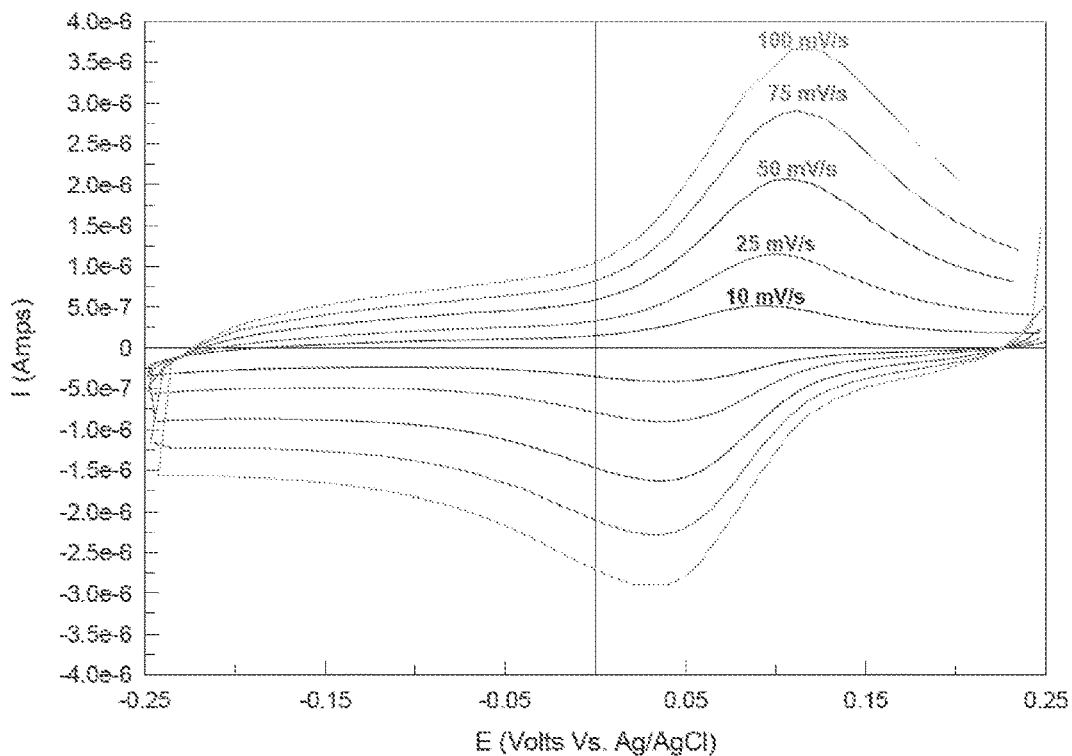

FIGS. 8A and 8B depict graphs illustrating output currents from mediator reduction in response to an input potential. The mediator was present as a polymer having structure (VI) (FIG. 8A) or (VII) (FIG. 8B). For each polymer, the mole fraction of x and y was presumed to be 0.1. A 5 mm glassy carbon electrode served as a working electrode (WE), Ag/AgCl as a reference electrode (RE), and platinum gauze as a counter electrode (CE). In FIG. 8A, the mediator composition was present at a concentration of 0.6 mg/mL in a mixture containing 10 mM PBS buffer (pH 7.4). In FIG. 8B, the mediator composition was present at a concentration of 0.504 mg/mL in a mixture containing 10 mM PBS buffer (pH 7.4). The concentrations of the polymers in their respective compositions were selected to provide approximately the same moles of phenothiazine groups in each composition. The mixtures were purged with nitrogen for 20 minutes before analysis using cyclic voltammetry. The input potential was scanned between −250 mV and 250 mV vs. Ag/AgCl. The rate of change of the input potential was varied from 10 mV/s to 100 mV/s, as indicated in FIGS. 8A and 8B.

Referring to FIG. 8A, the redox peak potential for the mediator composition including a polymer having structure (VI) was about +31 mV vs. Ag/AgCl. The oxidative and reductive peak separation was about 31.5 mV. This separation indicates that the reduction of this composition was a two-electron process, which is close to the theoretical limit of Nernstian behavior at 60 mV/2e. The diffusion coefficient for the polymer was calculated to be about $3.5 \times 10^{-8}$ cm$^2$/s, for both the oxidized and reduced forms of the functional groups.

Referring to FIG. 8B, the redox peak potential for the mediator composition including a polymer having structure (VII) was about +71 mV vs. Ag/AgCl. The oxidative and reductive peak separation was about 66 mV. This larger separation relative to that of the theoretical limit of Nernstian behavior may indicate some irreversibility in the oxidation and reduction of the functional groups of structure (VII). The diffusion coefficient for the polymer having reduced functional groups was calculated to be about $7 \times 10^{-8}$ cm$^2$/s, and the diffusion coefficient for the polymer having oxidized functional groups was calculated to be about $4 \times 10^{-8}$ cm$^2$/s.

A non-leaching mediator polymer that includes a polymeric backbone and a plurality of functional groups bonded to the polymeric backbone, where the functional groups may be oxidized or reduced, may include a polymer having the general formula (VIII):

ene glycol) group, or an α,ω-oxy-poly(propylene glycol) group. The R' group may include an aryl group, such as a bisphenol A group, a resorcinol group, a bisphenol A propoxy group, or a bis-(4-oxyphenyl) group. The R' group may include a siloxane group, such as an α,ω-2-ethoxy-poly (dimethylsiloxane) group. The R' group may include a mixture of these groups, and more than one type of R' group may be present in the polymer. Preferably the R' group is an alkyl group having from 1 to 10 carbon atoms, such as a methyl group, an ethyl group, a propyl group, or a butyl group. More preferably, the R' group is an alkyl group having from 1 to 6 carbon atoms or from 1 to 4 carbon atoms, and more preferably is an ethyl group.

A non-leaching mediator polymer may be made by reacting one or more compounds having general formula (I), (II) and/or (III) with a polymer having a precursor polymeric backbone and a plurality of nucleophilic groups bonded to the precursor polymeric backbone. Examples of nucleophilic groups that may be bonded to the precursor polymeric backbone include thiol groups, cyano groups, alcohol groups, carboxylate groups, amino groups and amido groups.

Examples of polymers having a precursor polymeric backbone and a plurality of nucleophilic groups bonded to the precursor polymeric backbone include polymers and copolymers formed from monomers containing nucleophilic groups, including N-thioethyl acrylamide, N,N'-cystamine bisacrylamide, cyanoacrylate, acrylonitrile, vinyl alcohol, hydroxystyrene, vinyl acetate, acrylic acid, methacrylic acid, aminoethyl methacrylate, vinyl pyridine, 4-vinylpyridine-N-oxide, allylamine, ethyleneimine, diallylmethylam-

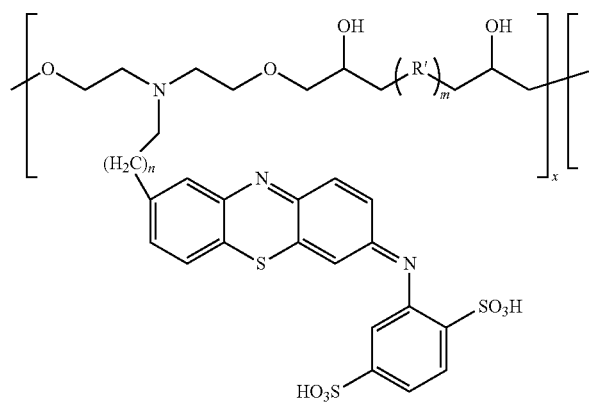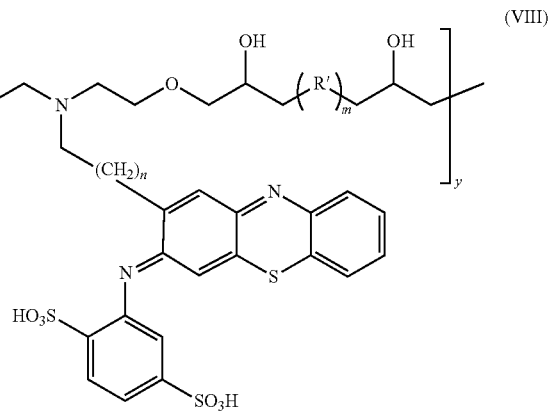

(VIII)

and salts thereof, where R' is an organic group, where m is 0 or 1, where n is about 9, and where x and y independently are an integer from 1 to 10,000.

Preferably, the sum of x and y in the polymer having the general formula (VIII) is from 10 to 10,000. More preferably the sum of x and y is from 20 to 1,000. Preferably x and y independently are an integer from 1 to 70. More preferably x and y independently are an integer from 2 to 20, and more preferably are an integer from 30 to 10.

Preferably m is 1, and R' is an organic group in the polymer having the general formula (VIII). The R' group may include an aliphatic group, such as a methyl group, an ethyl group, a propyl group, a butyl group, 1,4-butanedioxy group, a 1,3-butanedioxy group, a 1,4-cycloheanedimethoxy group, a 1,3-dioxy-2-propanol group, a diethylene glycoxy group, a neopentyl glycoxy group, an α,ω-oxy-poly(ethyline, lysine and/or acrylamide. Copolymers formed from the above monomers preferably are formed from mixtures of the monomers containing nucleophilic groups and monomers without the nucleophilic groups. Examples of polymers having a precursor polymeric backbone and a plurality of nucleophilic groups bonded to the precursor polymeric backbone also include cellulose and its derivatives, including carboxymethyl cellulose, ethyl cellulose and cellulose acetate. Presently preferred polymers having a precursor polymeric backbone and a plurality of nucleophilic groups bonded to the precursor polymeric backbone include poly (β-carboxyl-γ-(2-mercaptoethyl)carbamoyl-butene), poly (diallyl-methylamine) hydrochloride, 4-vinylpyridine-N-oxide, poly(allylamine) and poly(ethyleneimine).

Figure 9:
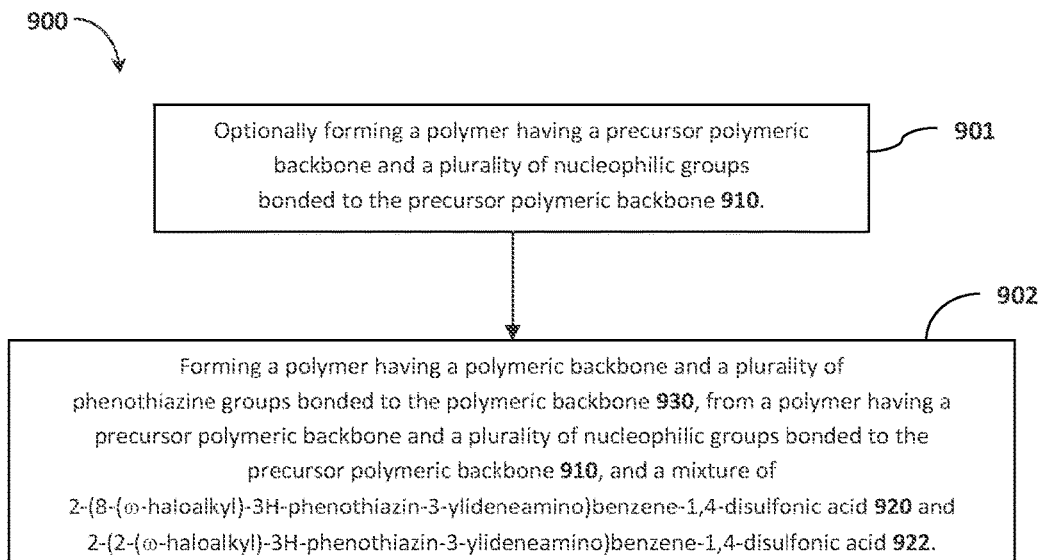
FIG. 9 depicts a method for making a polymer.

FIG. 9 depicts a method 900 of making a polymer. The method 900 includes forming 902 a polymer having a polymeric backbone and a plurality of phenothiazine groups bonded to the polymeric backbone 930, from a polymer having a precursor polymeric backbone and a plurality of nucleophilic groups bonded to the precursor polymeric backbone 910, and a mixture of 2-(8-(ω-haloalkyl)-3H-phenothiazin-3-ylideneamino)benzene-1,4-disulfonic acid 920 and 2-(2-(ω-haloalkyl)-3H-phenothiazin-3-ylideneamino)benzene-1,4-disulfonic acid 922. The method 900 optionally includes forming 901 a polymer having a precursor polymeric backbone and a plurality of nucleophilic groups bonded to the precursor polymeric backbone 910. The polymer 930 may be, for example, a polymer having the general formula (VI) or a polymer having the general formula (VII).

Reactants 920 and 922 correspond to compounds 376 and 378 of FIG. 3, respectively. Preferably the 2-(8-(ω-haloalkyl)-3H-phenothiazin-3-ylideneamino)benzene-1,4-disulfonic acid 920 is a 2-(8-(ω-bromoalkyl)-3H-phenothiazin-3-ylideneamino)benzene-1,4-disulfonic acid, and more preferably is 2-(8-(10-bromodecyl)-3H-phenothiazin-3-ylideneamino)benzene-1,4-disulfonic acid (see 476 of FIG. 4). Preferably the 2-(2-(ω-haloalkyl)-3H-phenothiazin-3-ylideneamino)benzene-1,4-disulfonic acid 922 is a 2-(2-(ω-bromoalkyl)-3H-phenothiazin-3-ylideneamino)benzene-1,4-disulfonic acid, and more preferably is 2-(2-(10-bromodecyl)-3H-phenothiazin-3-ylideneamino)benzene-1,4-disulfonic acid (see 478 of FIG. 4).

Figure 10A:
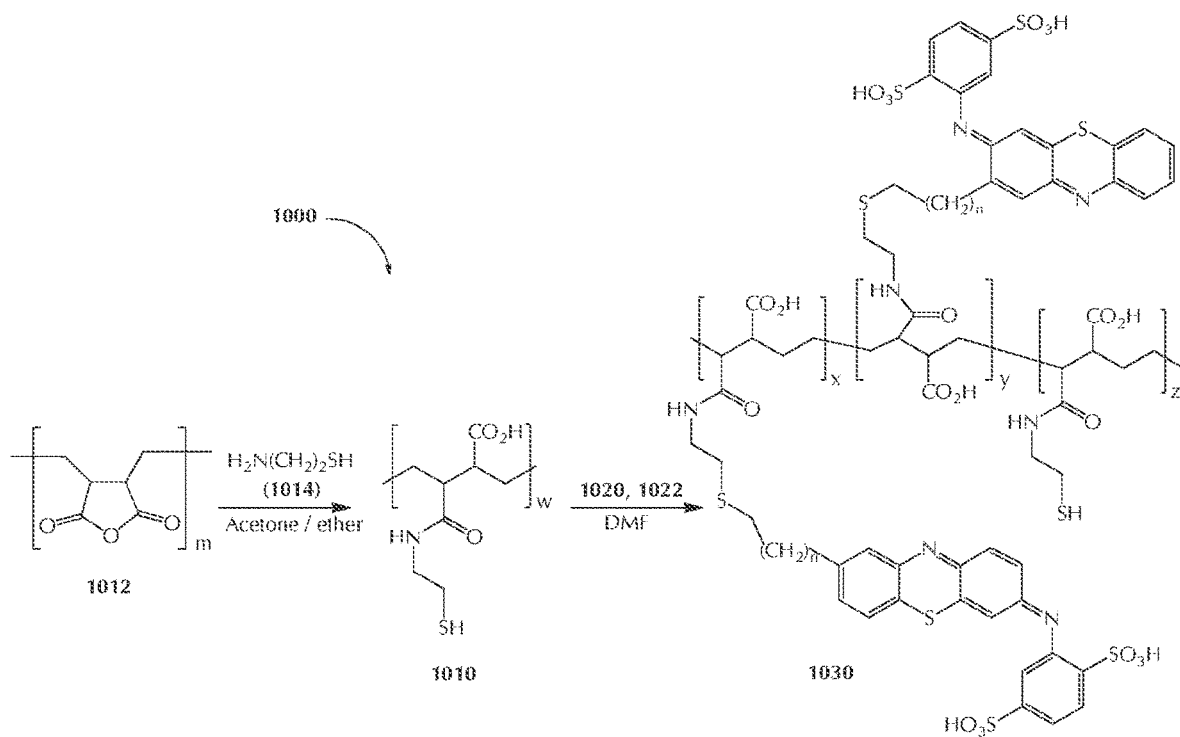
FIGS. 10A and 10B depict chemical structures and reaction schemes for methods of making a composition that includes a polymer having the general formula (VI) (FIG. 10A) or a polymer having the general formula (VII) (FIG. 10B).

FIG. 10A depicts chemical structures and reaction schemes for a method 1000 of making a composition including a polymer having the general formula (VI). Method 1000 includes forming poly(β-carboxyl-γ-(2-mercaptoethyl)carbamoyl-butene) 1010 from poly(ethylene-alt-maleic anhydride) 1012 and 2-aminoethanethiol hydrochloride 1014. The polymer 1010 includes thiol groups (—SH) as the plurality of nucleophilic groups bonded to the precursor polymeric backbone. Method 1000 further includes forming polymer 1030 from a mixture of the poly(β-carboxyl-γ-(2-mercaptoethyl)carbamoyl-butene) 1010, 2-(8-(ω-bromoalkyl)-3H-phenothiazin-3-ylideneamino)benzene-1,4-disulfonic acid 1020 and 2-(2-(ω-bromoalkyl)-3H-phenothiazin-3-ylideneamino)benzene-1,4-disulfonic acid 1022. Reactants 1020 and 1022 are examples of compounds 376 and 378 of FIG. 3, respectively.

In one example, 2-aminoethanethiol hydrochloride 1014 (5.50 g of 90% pure material, 43.8 mmol) was suspended in ether (50 mL) under a nitrogen atmosphere. A solution of triethylamine (39.7 mmol, 4.01 g, 5.53 mL) in ether (20 ml) was added dropwise to the suspension over fifteen minutes to form a first reaction mixture. The first reaction mixture was stirred overnight and was then filtered. The filtered mixture was added to a solution of poly(ethylene-alt-maleic anhydride) 1012 (PEMA; molecular weight of 100,000-500,000 daltons, 5 g, 40 mmol) in acetone (70 mL) to form a second reaction mixture. The mixture was stirred overnight before removing the precipitate by filtration. The precipitate was washed with acetone (50 ml), stirred in fresh acetone (50 ml) for ten minutes and filtered. The solid was dried in a vacuum oven for 48 hours to provide poly(β-carboxyl-γ-(2-mercaptoethyl)-carbamoyl-butene) 1010 as a pale yellow solid (6.15 g; 76% yield).

Polymer 1010 was then suspended in dimethyl formamide (DMF; 2 mL) and stirred for 1 hour. A mixture of 2-(8-(10-bromodecyl)-3H-phenothiazin-3-ylideneamino)benzene-1,4-disulfonic acid (see 1020 and 476) and 2-(2-(10-bromodecyl)-3H-phenothiazin-3-ylideneamino)benzene-1,4-disulfonic acid (see 1022 and 478) (17 mg, 23.9 micromoles) was added to the suspension to form a reaction mixture. The reaction mixture was stirred at ambient temperature for 1 week, and was then diluted with 4 mL water and transferred to SnakeSkin® dialysis tubing having a molecular weight cutoff (MWCO) of 7,000 daltons and containing 1 mL of water. The dialysis tubing was closed with a clip and placed in a 2 L beaker containing 1,600 mL water. The water was gently stirred for 2-3 days before being exchanged with fresh water. Each time the water was exchanged, a sample of the liquid in the dialysis tubing was analyzed by thin layer chromatography (TLC; silica, methanol:ethyl acetate ratio of 9:1) to test for the presence of 1020 and 1022. After 3 exchanges with fresh water, the water was exchanged with a 3-5% brine solution. The brine was exchanged every 2-3 days, and the process repeated 6 times. The dialysis took approximately 3 weeks in total until there was no detectable 1020 or 1022 in the liquid in the dialysis tubing. The brine was then exchanged with water, and the stirring continued for two hours. The water was exchanged with fresh water 5 times to remove any sodium chloride from inside the dialysis tubing. The liquid was removed from the dialysis tubing and used without further purification as a mixture containing polymer 1030.

Figure 10B:
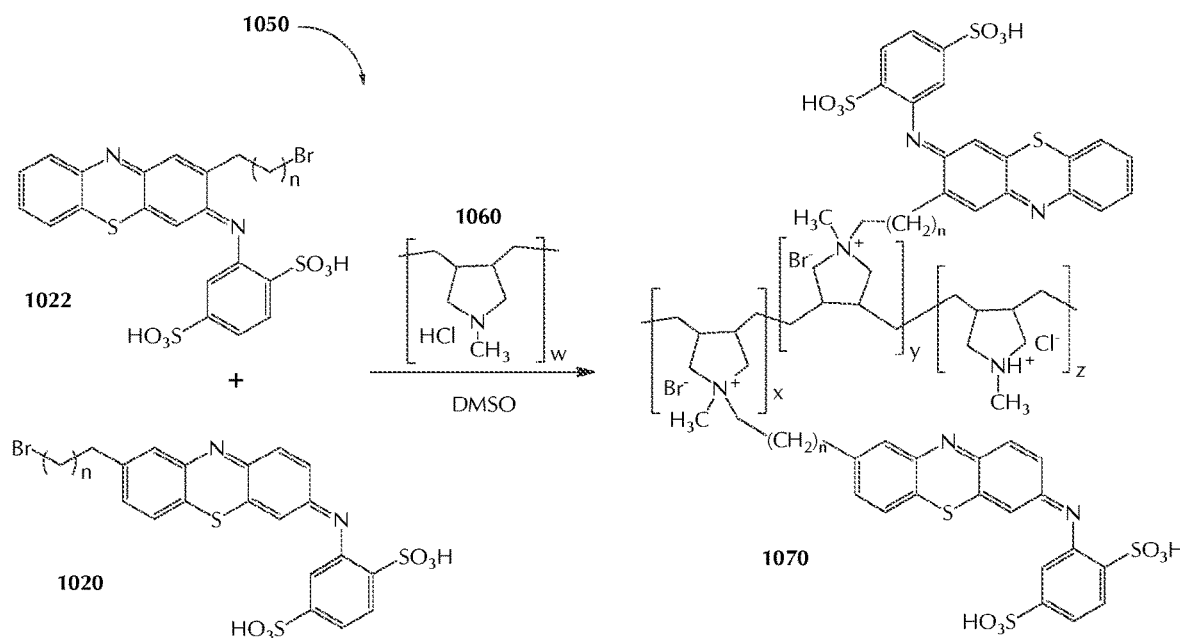

FIG. 10B depicts chemical structures and reaction schemes for a method 1050 of making a composition including a polymer having the general formula (VII). Method 1050 includes forming polymer 1070 from a mixture of poly(diallyl-methylamine) hydrochloride 1060, 2-(8-(ω-bromoalkyl)-3H-phenothiazin-3-ylideneamino)benzene-1,4-disulfonic acid 1020 and 2-(2-(ω-bromoalkyl)-3H-phenothiazin-3-ylideneamino)benzene-1,4-disulfonic acid 1022. The polymer 1060 includes amine groups ($R_2N$—$CH_3$) as the plurality of nucleophilic groups bonded to the precursor polymeric backbone. Reactants 1020 and 1022 are examples of compounds 376 and 378 of FIG. 3, respectively.

In one example, a mixture of 2-(8-(10-bromodecyl)-3H-phenothiazin-3-ylideneamino)benzene-1,4-disulfonic acid (see 1020 and 476) and 2-(2-(10-bromodecyl)-3H-phenothiazin-3-ylideneamino)benzene-1,4-disulfonic acid (see 1022 and 478) (20 mg, 28.1 micromoles) was weighed into a 5 mL vial and dissolved in DMSO (2 mL). Poly(diallylmethylamine) hydrochloride 1060 having a molecular weight of 20,000 daltons (100 microliters of 50% solution in water, 2.5 micromoles) was added in one portion to the mixture of 1020 and 1022 to form a reaction mixture. The reaction mixture was stirred at ambient temperature for 1 week, and was then transferred to SnakeSkin® dialysis tubing having a MWCO of 7,000 daltons and containing 2 mL of water. The dialysis tubing was closed with a clip and placed in a 2 L beaker containing 1,600 mL water. The water was gently stirred for 2-3 days before being exchanged with fresh water. Each time the water was exchanged, a sample of the liquid in the dialysis tubing was analyzed by TLC (silica, methanol:ethyl acetate ratio of 9:1) to test for the presence of 1020 and 1022. After 3 exchanges with fresh water, the water was exchanged with a 3-5% brine solution. The brine was exchanged every 2-3 days, and the process repeated 30 times. The dialysis took approximately 11 weeks in total until there was no detectable 1020 or 1022 in the liquid in the dialysis tubing. The brine was then exchanged with water, and the stirring continued for two hours. The water was exchanged with fresh water 5 times to remove any sodium chloride from inside the dialysis tubing. The liquid was removed from the dialysis tubing and used without further purification as a mixture containing polymer 1070.

A non-leaching mediator polymer may be made by reacting one or more compounds having general formula (IX):

(IX)

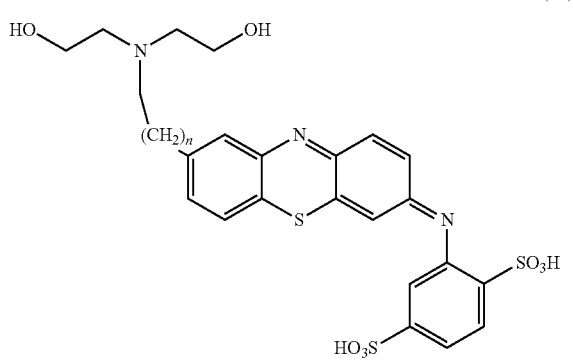

and/or having general formula (X):

(X)

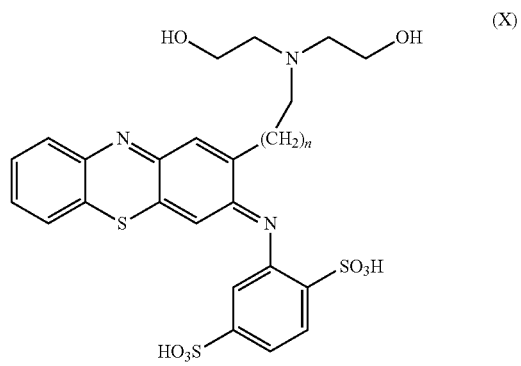

or salts thereof, with a compound having a plurality of polymerizable groups. In formulas (IX) and (X), n is about 9. Examples of polymerizable groups include epoxide groups, isocyanate groups, carboxylic acid groups, and anhydride groups.

Figure 11:
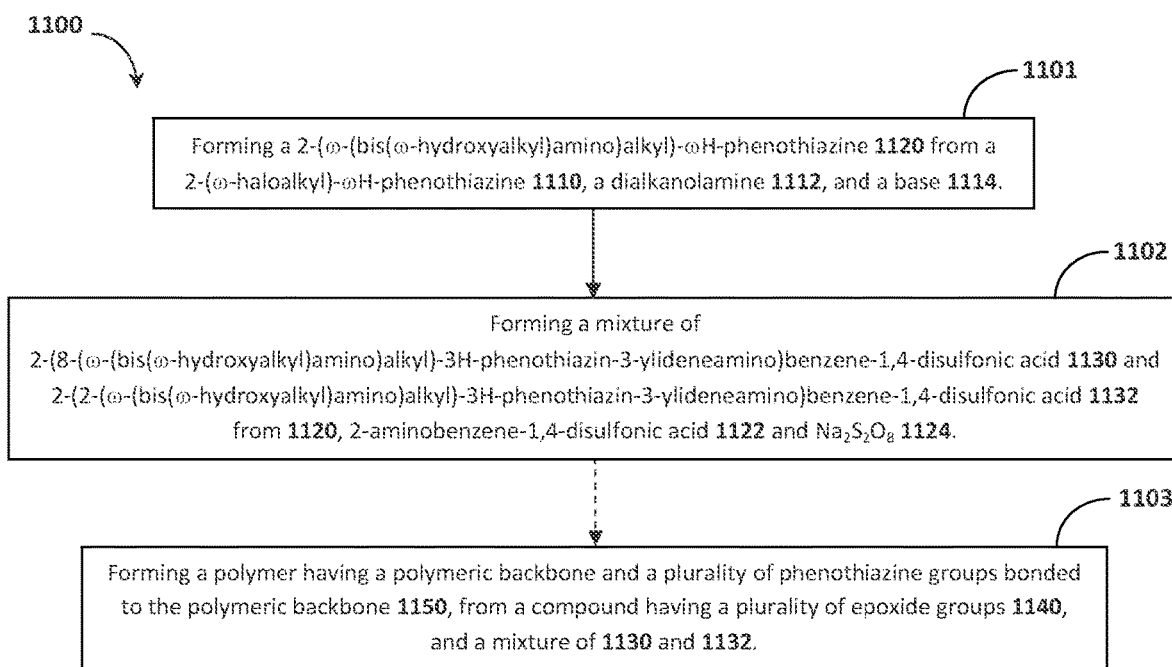
FIG. 11 depicts a method for making a method for making a composition including at least one compound having the general formula (IX) or (X), and a method for making a polymer.

FIG. 11 depicts a method 1100 of making a composition including at least one compound having the general formula (IX) or (X) and salts thereof. The method 1100 includes forming 1101 a 2-(ω-(bis(ω-hydroxyalkyl)amino)alkyl)-ωH-phenothiazine 1120 from a 2-(ω-haloalkyl)-ωH-phenothiazine 1110, a dialkanolamine 1112, and a base 1114; and forming 1102 a mixture of 2-(8-(ω-(bis(ω-hydroxyalkyl)amino)alkyl)-3H-phenothiazin-3-ylideneamino)benzene-1,4-disulfonic acid 1130 and 2-(2-(ω-(bis(ω-hydroxyalkyl)amino)alkyl)-3H-phenothiazin-3-ylideneamino)benzene-1,4-disulfonic acid 1132 from 1120, 2-aminobenzene-1,4-disulfonic acid 1122 and $Na_2S_2O_8$ 1124. Products 1130 and 1132 are examples of compounds having the general formula (IX) and (X), respectively.

Preferably the 2-(8-(ω-(bis(ω-hydroxyalkyl)amino)alkyl)-3H-phenothiazin-3-ylideneamino)benzene-1,4-disulfonic acid 1130 is a 2-(8-(ω-(bis(2-hydroxyethyl)amino)alkyl)-3H-phenothiazin-3-ylideneamino)benzene-1,4-disulfonic acid, and more preferably is 2-(8-(10-(bis-2-hydroxyethylamino)alkyl)-3H-phenothiazin-3-ylideneamino)benzene-1,4-disulfonic acid. Preferably the 2-(2-(ω-(bis(ω-hydroxyalkyl)amino)alkyl)-3H-phenothiazin-3-ylideneamino)benzene-1,4-disulfonic acid 1132 is a 2-(2-(ω-(bis-2-hydroxyethylamino)alkyl)-3H-phenothiazin-3-ylideneamino)benzene-1,4-disulfonic acid, and more preferably is 2-(2-(10-(bis-2-hydroxyethylamino)alkyl)-3H-phenothiazin-3-ylideneamino)benzene-1,4-disulfonic acid.

FIG. 11 also depicts a method 1103 of forming a polymer having a polymeric backbone and a plurality of phenothiazine groups bonded to the polymeric backbone 1150, from a diepoxide 1140, and a mixture of 2-(8-(ω-(bis(ω-hydroxyalkyl)amino)alkyl)-3H-phenothiazin-3-ylideneamino)benzene-1,4-disulfonic acid 1130 and 2-(2-(ω-(bis(ω-hydroxyalkyl)amino)alkyl)-3H-phenothiazin-3-ylideneamino)benzene-1,4-disulfonic acid 1132. The polymer 1150 may be, for example, a polymer having the general formula (VIII). Preferably the diepoxide 1140 is a diepoxyalkane, and more preferably is 1,2,7,8-diepoxyoctane.

Figure 12:
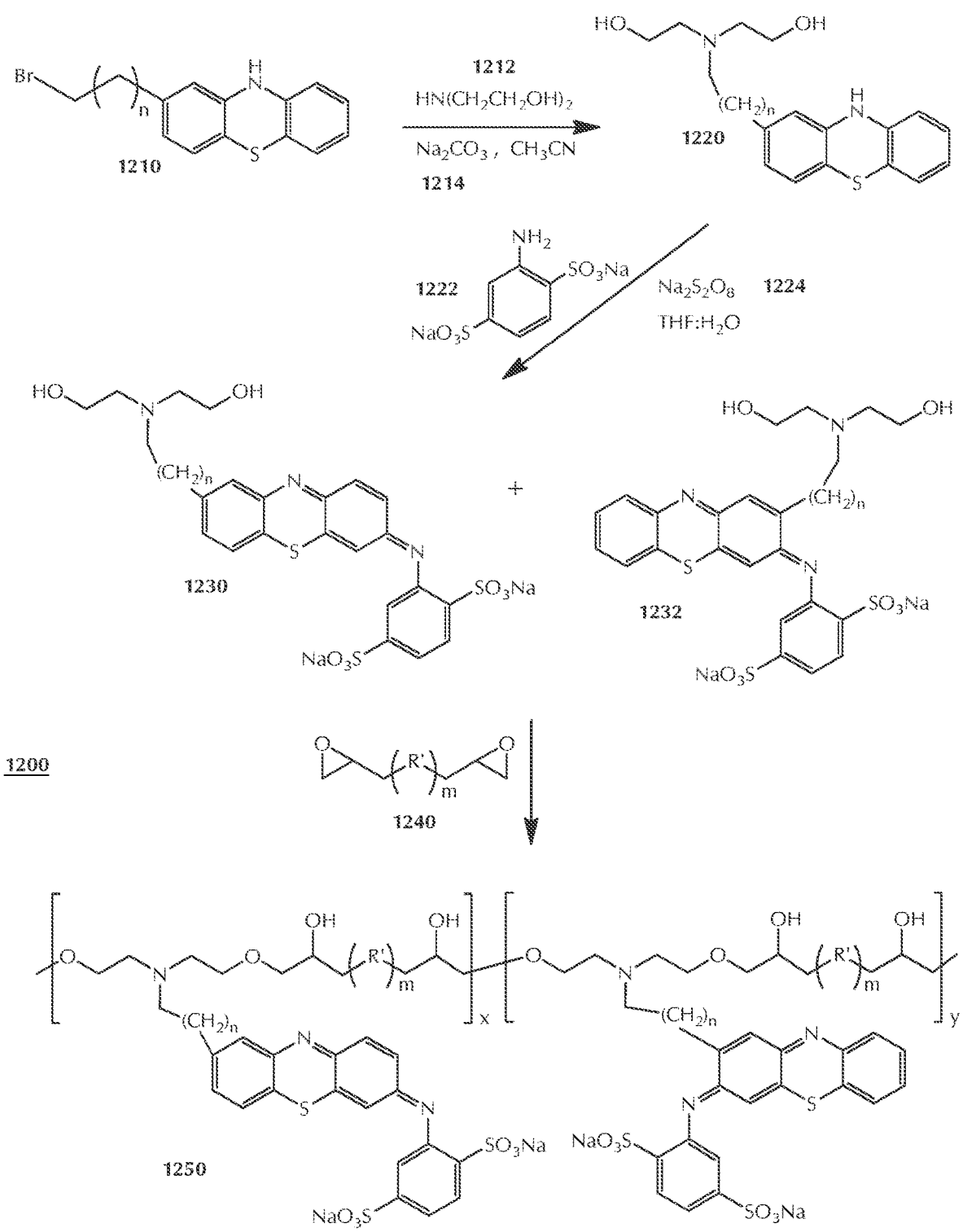
FIG. 12 depicts chemical structures and reaction schemes for a method of making a composition that includes a polymer having the general formula (VIII).

FIG. 12 depicts chemical structures and reaction schemes for a method 1200 of a) making a composition including at least one compound having the general formula (IX) or (X) and salts thereof, and b) making a composition including a polymer having the general formula (VIII). Method 1200 includes forming 2-(ω-(bis-2-hydroxyethylamino)alkyl)-ωH-phenothiazine 1220 from 2-(ω-bromoalkyl)-ωH-phenothiazine 1210, diethanolamine 1212, and sodium carbonate 1214. Reactant 1210 is an example of compound 372 of FIG. 3. Method 1200 further includes forming a mixture of 2-(8-(ω-(bis-2-hydroxyethylamino)alkyl)-3H-phenothiazin-3-ylideneamino)benzene-1,4-disulfonic acid 1230 and 2-(2-(ω-(bis-2-hydroxyethylamino)alkyl)-3H-phenothiazin-3-ylideneamino)benzene-1,4-disulfonic acid 1232 from the 2-(ω-(bis-2-hydroxyethylamino)alkyl)-ωH-phenothiazine 1220, 2-aminobenzene-1,4-disulfonic acid 1222 and $Na_2S_2O_8$ 1224. Products 1230 and 1232 are examples of compounds having the general formula (IX) and (X), respectively.

Method 1200 of FIG. 12 further includes forming polymer 1250 from the mixture of 2-(8-(ω-(bis-2-hydroxyethylamino)alkyl)-3H-phenothiazin-3-ylideneamino)benzene-1,4-disulfonic acid 1230 and 2-(2-(ω-(bis-2-hydroxyethylamino)alkyl)-3H-phenothiazin-3-ylideneamino)benzene-1,4-disulfonic acid 1232 and a diepoxide 1240.

In one example, 2-(10-bromodecyl)-ωH-phenothiazine (1210) was combined with diethanolamine 1212 (1.1 equivalents), and sodium carbonate 1214 (2.2 equivalents) in acetonitrile to form a first reaction mixture, and the first reaction mixture was heated at reflux overnight. An aqueous workup of the reaction mixture yielded 2-(10-(bis-2-hydroxyethylamino)decyl)-ωH-phenothiazine (1220) in nearly quantitative yield (97% purity by high-performance liquid chromatography (HPLC)). The product was added to a solution of 2-aminobenzene-1,4-disulfonic acid 1222 and $Na_2S_2O_8$ 1224 in a mixture of THF and water to form a second reaction mixture, and product was present by liquid chromatograph/mass spectrometry (LCMS) after 30 minutes at room temperature. The second reaction mixture was poured into a saturated aqueous sodium bicarbonate solution, yielding a precipitate that was isolated by filtration. The precipitate was determined to be a mixture of 2-(8-(10-(bis-2-hydroxyethylamino)decyl)-3H-phenothiazin-3-ylideneamino)benzene-1,4-disulfonic acid (1230) and 2-(2-(10-(bis-2-hydroxyethylamino)decyl)-3H-phenothiazin-3-ylideneamino)benzene-1,4-disulfonic acid (1232) by LCMS. The purity of the mixed product was 83%, with a total yield of 33%.

The mixture of 2-(8-(10-(bis-2-hydroxyethylamino)decyl)-3H-phenothiazin-3-ylideneamino)benzene-1,4-disulfonic acid (1230) and 2-(2-(10-(bis-2-hydroxyethylamino)decyl)-3H-phenothiazin-3-ylideneamino)benzene-1,4-disulfonic acid (1232) was dissolved in THF and treated with sodium hydride (NaH, 2.2 equivalents) and stirred for 10 minutes at room temperature. The diepoxide (1240)

1,2,7,8-diepoxyoctane (1.1 equivalents) was then added to form a third reaction mixture, which was heated at 55° C. for one week. Analysis of a sample of the third reaction mixture by TLC showed a baseline spot having a low intensity, the continued presence of the starting material, and some streaks close to the starting material. The third reaction mixture was heated to 55° C. again for an additional week, and subsequent analysis by TLC was similar to the first analysis, except that the baseline spot was slightly more intense. The third reaction mixture was then heated to reflux for one week, and subsequent analysis by TLC showed no change from the previous analysis. The precipitate was isolated and dissolved in water, yielding a red aqueous solution and a residual insoluble precipitate. The aqueous solution was believed to contain polymer 1250.

A non-leaching mediator polymer may be made by reacting a polymer having a precursor polymeric backbone and a plurality of reactive functional groups bonded to the precursor polymeric backbone, with a compound having a first functional group that may be oxidized or reduced and having a second functional group that can react with the reactive functional groups bonded to the precursor polymeric backbone. The compound having a first functional group that may be oxidized or reduced and having a second functional group that can react with the reactive functional groups bonded to the precursor polymeric backbone may be a polymer bondable mediator. A polymer bondable mediator includes a mediator that can be bonded to a polymer.

Compounds having the general formulas (I), (II) and/or (III) may be useful as polymer bondable mediators. The terminal halogen group may be reacted with a functional group of a polymer, bonding the mediator to the polymer. Bonding includes covalent bonding where an electron pair is shared between two atoms. The terminal halogen group may be converted into a different functional group, and this modified mediator may then be bonded to a polymer. The polymer may be a binder of a reagent composition for an electrochemical biosensor.

Figure 13:
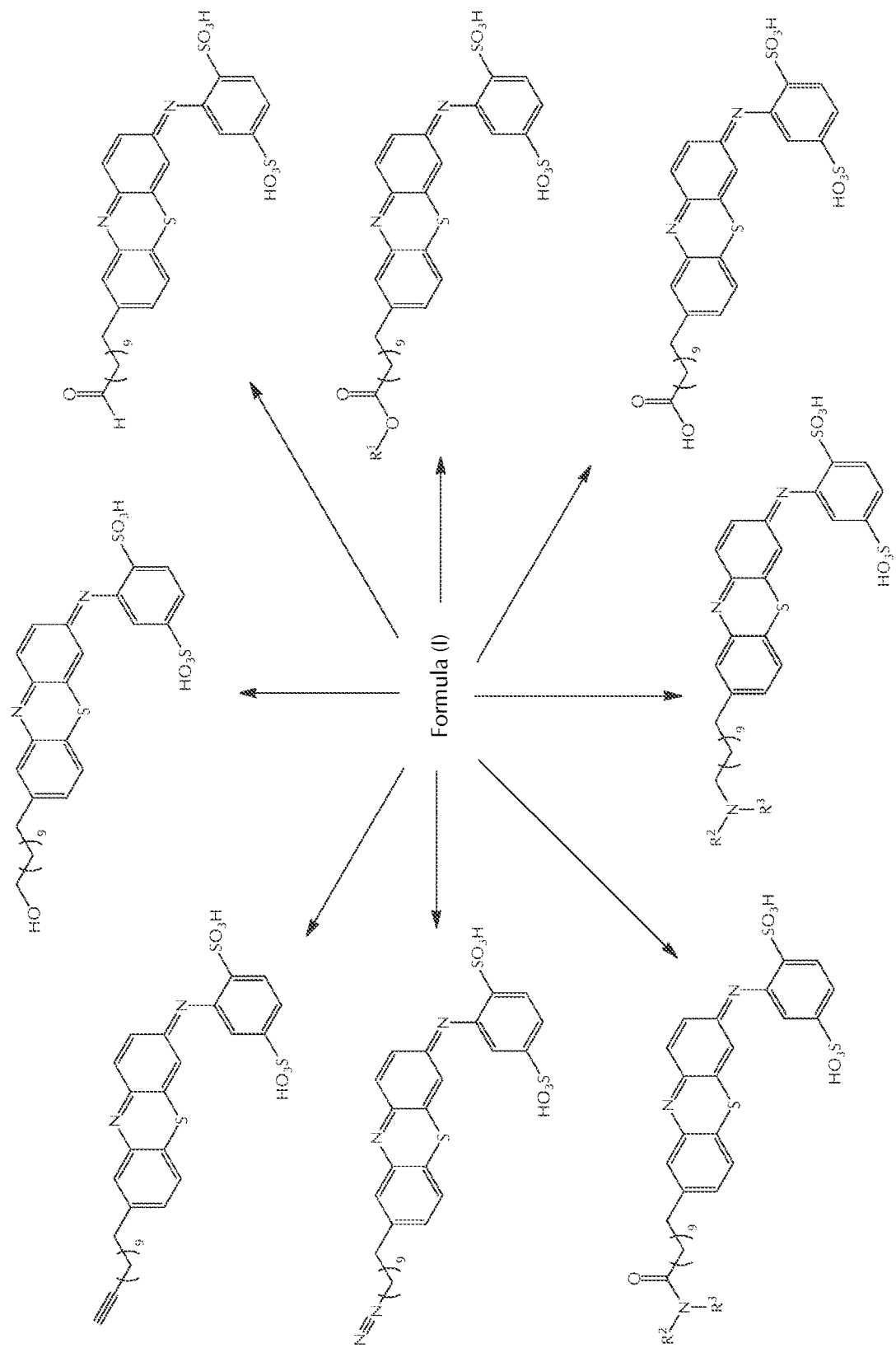
FIG. 13 depicts examples of polymer bondable mediators having terminal functional groups other than halogen.

FIG. 13 depicts examples of polymer bondable mediators having terminal functional groups other than halogen. These examples are based on compounds having the general formula (I); however, similar derivatives of compounds having the general formulas (II) or (III) are envisioned. The exemplary terminal functional groups depicted in FIG. 13 are, clockwise from top, hydroxyl, aldehyde, ester ($R^1$=organic group), carboxylic acid, amine, amide, azide and alkyne groups.

A non-leaching mediator polymer may be made by polymerizing monomers, where the monomers include a compound having a first functional group that may be oxidized or reduced and having a second functional group that can participate in a polymerization or copolymerization reaction. The compound having a first functional group that may be oxidized or reduced and having a second functional group that can participate in a polymerization or copolymerization reaction may be a polymerizable mediator. A polymerizable mediator includes a mediator that can polymerize to form a polymer, or that can copolymerize with other monomers to form a copolymer.

Compounds having the general formulas (I), (II) and/or (III) may be useful as intermediates for preparing polymerizable mediators. The terminal halogen group may be converted into a functional group capable of polymerization or copolymerization. For example, the terminal halogen may be converted into a carbon-carbon double or triple bond. This modified mediator having a terminal unsaturated group may then polymerize or copolymerize through radical, anionic and/or cationic polymerization. The terminal halogen also may be converted into a functional group that can undergo a condensation reaction. This modified mediator having a terminal functional group may then polymerize or copolymerize through a condensation polymerization. The resulting polymer may be used as a binder of a reagent composition for an electrochemical biosensor.

Figure 14:
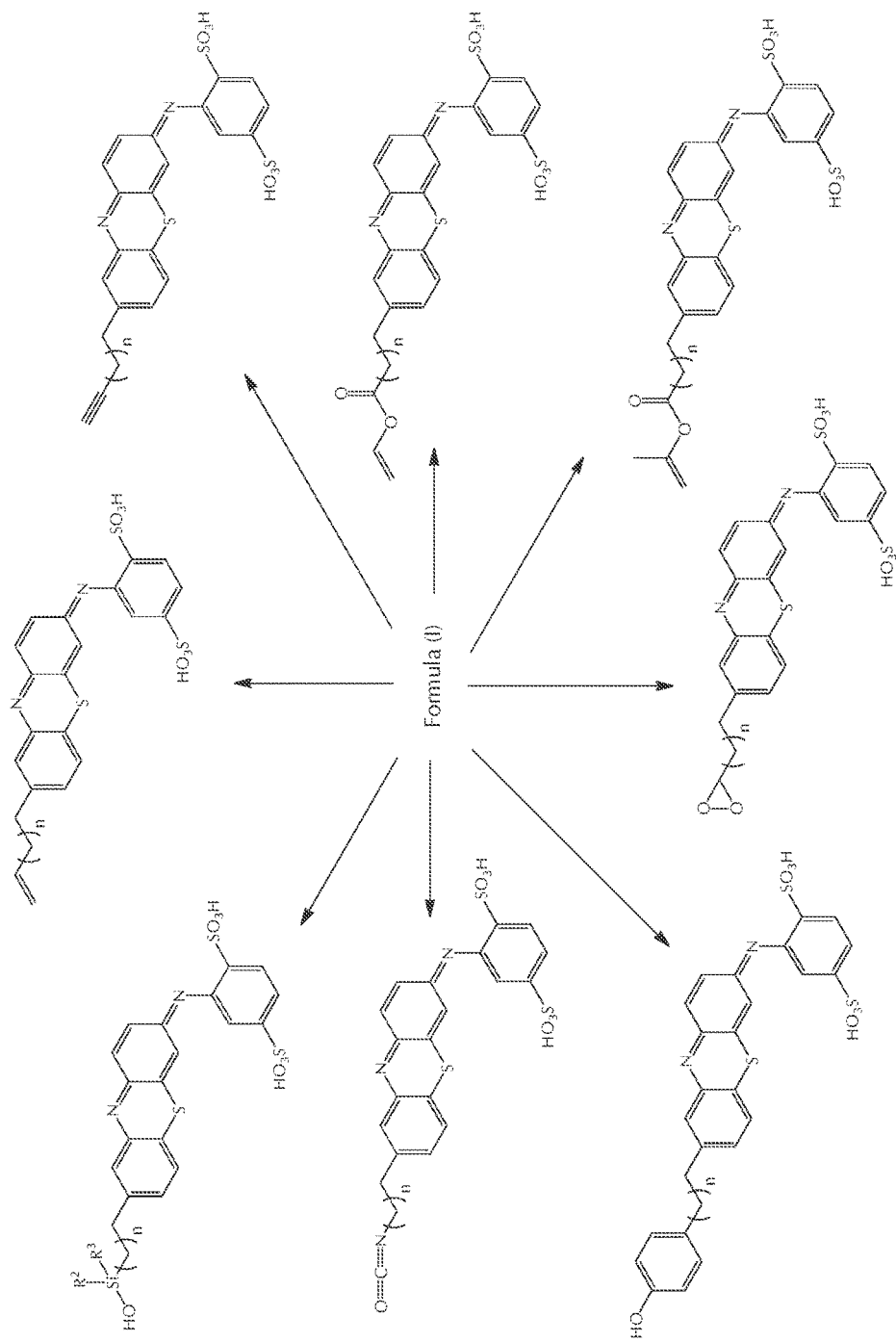
FIG. 14 depicts examples of polymerizable mediators having terminal functional groups other than halogen.

FIG. 14 depicts examples of polymerizable mediators having terminal functional groups other than halogen. These examples are based on compounds having the general formula (I); however, similar derivatives of compounds having the general formulas (II) or (III) are envisioned. The exemplary terminal functional groups depicted in FIG. 14 are, clockwise from top, alkene, alkyne, acrylate, methacrylate, epoxide, phenol, isocyanate and silanol groups ($R^2$, $R^3$=organic groups).

The examples depicted in FIG. 14 also may be used as polymer bondable mediators, depending on the functional groups bonded to the precursor polymeric backbone. Likewise, the examples depicted in FIG. 13 also may be used as polymerizable mediators, depending on the polymerization reaction conditions and/or on the copolymerization reactivity of other monomers. In one example, a mediator having a terminal alkyne group is depicted in both FIG. 13 and in FIG. 14. In another example, a compound having the general formula (IX) or (X) is a species of the mediator having a terminal amine group depicted in FIG. 13.

Compounds having the general formulas (I), (II) and/or (III) also may be useful as surface active mediators. A surface active mediator is a non-bonded mediator that includes a hydrophobic portion and a hydrophilic portion. For compounds having the general formulas (I), (II) and/or (III), the alkyl chain group may function as the hydrophobic portion, whereas the benzene 1,4-disulfonic acid group may function as the hydrophilic portion. The compounds also may be modified by converting the terminal halogen group into a more hydrophobic group, such as an alkyl group, to further increase the difference in solubility of the two portions of the mediators.

Polymer bondable mediators, polymerizable mediators and/or surface active mediators may be used to provide immobilized mediators for electrochemical bioanalysis. While the benzene 1,4-disulfonic acid group of the compound may be sufficiently solubilized in an aqueous sample to interact with an analyte and/or an enzyme, the alkyl chain group of the compound may have a solubility in the sample that is so low as to inhibit the entire compound from dissolving in the sample. The overall solubility of the mediator may be further diminished when the mediator is bonded to a polymer. Thus, compounds having the general formulas (I), (II) and/or (III), derivatives of these compounds bonded to a polymer, polymers having a polymeric backbone and a plurality of phenothiazine groups bonded to the polymeric backbone, and/or polymers having structure (VI) or (VII) may be useful as mediators having little or no ability to leach into a sample.

While various embodiments of the invention have been described, it will be apparent to those of ordinary skill in the art that other embodiments and implementations are possible within the scope of the invention. Accordingly, the invention is not to be restricted except in light of the attached claims and their equivalents.

What is claimed is:

1. An electrochemical test sensor comprising a working electrode, a counter electrode and a mediator, the mediator including a polymer, the polymer including a polymeric backbone, and a plurality of phenothiazine groups bonded to the polymeric backbone;

where the plurality of phenothiazine groups includes at least one of a phenothiazine group having the general formula (IV):

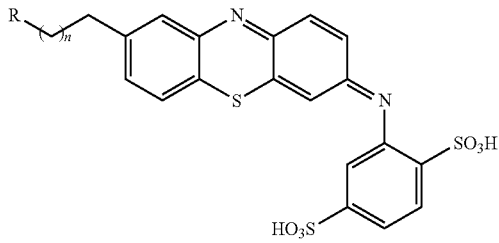

(IV)

and salts thereof, where n is about 9 and "R" represents the polymeric backbone to which the phenothiazine group is bonded, and a phenothiazine group having the general formula (V):

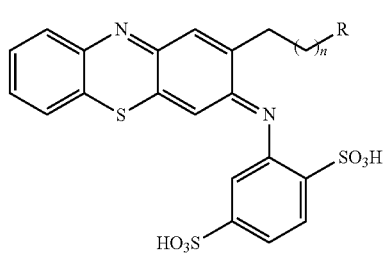

(V)

and salts thereof, where n is about 9 and "R" represents the polymeric backbone to which the phenothiazine group is bonded.

2. The electrochemical test sensor of claim 1, wherein the phenothiazine group is bonded to the polymeric backbone through a carbon-heteroatom bond.

3. The electrochemical test sensor of claim 1, wherein the phenothiazine group is bonded to the polymeric backbone through a group selected from the group consisting of an ether group, an ester group, a carbonate group, a urea group, a urethane group, an amine group, an amide group, a thioether group, a thiourea group and a sulfonamide group.

4. The electrochemical test sensor of claim 3, wherein the phenothiazine group is bonded to the polymeric backbone through a group selected from an ether group or an ester group.

5. The electrochemical test sensor of claim 3, wherein the phenothiazine group is bonded to the polymeric backbone through a carbonate group.

6. The electrochemical test sensor of claim 3, wherein the phenothiazine group is bonded to the polymeric backbone through a urea group or a urethane group.

7. The electrochemical test sensor of claim 3, wherein the phenothiazine group is bonded to the polymeric backbone through an amine group or an amide group.

8. The electrochemical test sensor of claim 3, wherein the phenothiazine group is bonded to the polymeric backbone through a thioether group or a thiourea group.

9. The electrochemical test sensor of claim 3, wherein the phenothiazine group is bonded to the polymeric backbone through a sulfonamide group.

10. The electrochemical test sensor of claim 1 further including glucose oxidase.

11. The electrochemical test sensor of claim 1 further including glucose dehydrogenase.

12. An electrochemical test sensor comprising a working electrode, a counter electrode, glucose dehydrogenase, and a mediator, the mediator including a polymer, the polymer including a polymeric backbone, and a plurality of phenothiazine groups bonded to the polymeric backbone;

where the plurality of phenothiazine groups includes at least one of a phenothiazine group having the general formula (IV):

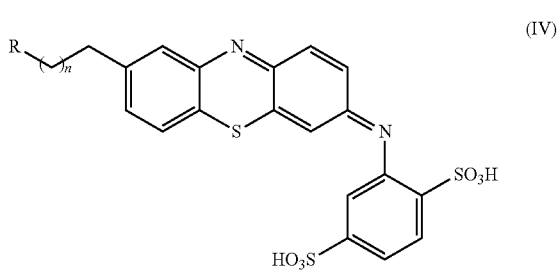

(IV)

and salts thereof, where n is about 9 and "R" represents the polymeric backbone to which the phenothiazine group is bonded, and a phenothiazine group having the general formula (V):

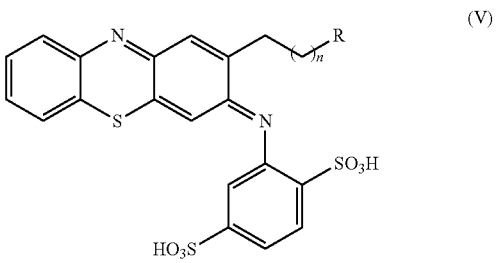

(V)

and salts thereof, where n is about 9 and "R" represents the polymeric backbone to which the phenothiazine group is bonded, wherein the phenothiazine group is bonded to the polymeric backbone through a carbon-heteroatom bond.

13. An electrochemical test sensor comprising a working electrode, a counter electrode, glucose oxidase, and a mediator, the mediator including a polymer, the polymer including a polymeric backbone, and a plurality of phenothiazine groups bonded to the polymeric backbone;

where the plurality of phenothiazine groups includes at least one of a phenothiazine group having the general formula (IV):

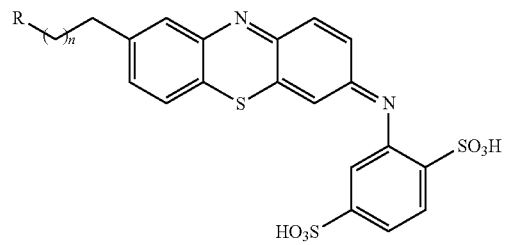

and salts thereof, where n is about 9 and "R" represents the polymeric backbone to which the phenothiazine group is bonded, and a phenothiazine group having the general formula (V):

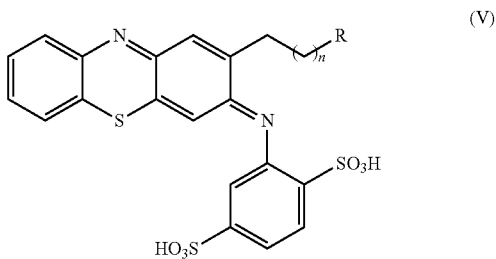

and salts thereof, where n is about 9 and "R" represents the polymeric backbone to which the phenothiazine group is bonded, wherein the phenothiazine group is bonded to the polymeric backbone through a carbon-heteroatom bond.

* * * * *